US008763082B2

(12) United States Patent
Huber et al.

(10) Patent No.: US 8,763,082 B2
(45) Date of Patent: Jun. 24, 2014

(54) INTERACTIVE CLIENT MANAGEMENT OF AN ACCESS CONTROL LIST

(75) Inventors: Kurt Donald Huber, Kennesaw, GA (US); Judson John Flynn, Decatur, GA (US); William Gordon Mansfield, Sugar Hill, GA (US)

(73) Assignee: AT&T Mobility II LLC, Atlanta, GA (US)

( * ) Notice: Subject to any disclaimer, the term of this patent is extended or adjusted under 35 U.S.C. 154(b) by 384 days.

(21) Appl. No.: 12/275,878

(22) Filed: Nov. 21, 2008

(65) Prior Publication Data

US 2009/0288145 A1 Nov. 19, 2009

Related U.S. Application Data

(60) Provisional application No. 61/052,813, filed on May 13, 2008.

(51) Int. Cl.
*H04L 29/06* (2006.01)
*H04W 12/08* (2009.01)

(52) U.S. Cl.
CPC ........... *H01L 63/101* (2013.01); *H04L 63/108* (2013.01); *H04W 12/08* (2013.01); *H04L 63/0876* (2013.01)
USPC .............. 726/3; 726/1; 380/270; 709/225; 455/411

(58) Field of Classification Search
CPC . H04L 63/0876; H04L 63/101; H04L 63/108; H04W 12/08
USPC ....... 726/1, 2, 3; 709/225; 380/270; 370/338; 455/411, 444, 525
See application file for complete search history.

(56) References Cited

U.S. PATENT DOCUMENTS

| 5,745,559 A | 4/1998 | Weir |
|---|---|---|
| 5,864,764 A | 1/1999 | Thro et al. |

(Continued)

FOREIGN PATENT DOCUMENTS

| CN | 101017554 A | 8/2007 |
|---|---|---|
| CN | 101175333 A | 5/2008 |

(Continued)

OTHER PUBLICATIONS

Hasan, Mohammad Masud; Huang, Xiaodong; Jue, Jason P.; "Survivable Wireless Access Network Design with Dual-homing Capabilities"; IEEE Global Telecommunications Conference, Nov. 27-Dec. 1, 2006, 5 pgs.*

(Continued)

*Primary Examiner* — Victor Lesniewski
(74) *Attorney, Agent, or Firm* — Amin, Turocy & Watson, LLP

(57) ABSTRACT

System(s) and method(s) provide access management to femtocell service through access control list(s) (e.g., white list(s)). Such white list(s) can be configured via a networked interface which facilitates access management to a femtocell. White list(s) includes a set of subscriber station(s) identifier numbers, codes or tokens, and also can include additional fields for femtocell access management based on desired complexity. Various example aspects such as white list(s) management, maintenance and dissemination; pre-configuration; and inclusion of wireless device(s) or subscriber(s) are also provided. An access management component can facilitate automatic population of a white list(s) associated with a femtocell and can prompt a communication device detected in the femtocell coverage area to inquire whether the communication device desires to connect to the femtocell, be entered into the white list(s), and access a services associated with the femtocell, on a permanent basis or temporarily for a specified period of time.

22 Claims, 17 Drawing Sheets

(56) References Cited

U.S. PATENT DOCUMENTS

| | | | |
|---|---|---|---|
| 6,052,594 A | 4/2000 | Chuang et al. | |
| 6,151,505 A | 11/2000 | Larkins | |
| 6,208,659 B1 | 3/2001 | Govindarajan et al. | |
| 6,219,786 B1 | 4/2001 | Cunningham et al. | |
| 6,256,504 B1 | 7/2001 | Tell et al. | |
| 6,266,537 B1 | 7/2001 | Kashitani et al. | |
| 6,295,454 B1 | 9/2001 | Havinis et al. | |
| 6,363,261 B1 | 3/2002 | Raghavan | |
| 6,483,852 B1 | 11/2002 | Jacquet et al. | |
| 6,484,096 B2 | 11/2002 | Wong | |
| 6,512,478 B1 | 1/2003 | Chien | |
| 6,710,651 B2 | 3/2004 | Forrester | |
| 6,718,023 B1 | 4/2004 | Zolotov | |
| 6,768,722 B1 | 7/2004 | Katseff et al. | |
| 7,080,139 B1 | 7/2006 | Briggs et al. | |
| 7,142,861 B2 | 11/2006 | Murai | |
| 7,146,153 B2 | 12/2006 | Russell | |
| 7,209,739 B1 | 4/2007 | Narayanabhatla | |
| 7,277,410 B2 | 10/2007 | Horneman | |
| 7,317,931 B2 | 1/2008 | Guo | |
| 7,370,356 B1 | 5/2008 | Guo | |
| 7,437,755 B2 | 10/2008 | Farino et al. | |
| 7,493,390 B2 | 2/2009 | Bobde et al. | |
| 7,496,383 B2 | 2/2009 | Kurata | |
| 7,509,124 B2 * | 3/2009 | O'Neil | 455/432.2 |
| 7,516,219 B2 | 4/2009 | Moghaddam et al. | |
| 7,558,251 B1 | 7/2009 | Huang et al. | |
| 7,574,731 B2 * | 8/2009 | Fascenda | 726/2 |
| 7,613,444 B2 | 11/2009 | Lindqvist et al. | |
| 7,614,078 B1 * | 11/2009 | Stieglitz | 726/2 |
| 7,623,857 B1 | 11/2009 | O'Neil | |
| 7,633,910 B2 * | 12/2009 | Zhun et al. | 370/338 |
| 7,751,826 B2 | 7/2010 | Gardner | |
| 7,761,526 B2 | 7/2010 | Pounds et al. | |
| 7,768,983 B2 | 8/2010 | Nylander et al. | |
| 7,853,265 B1 | 12/2010 | Ahmad et al. | |
| 7,885,644 B2 | 2/2011 | Gallagher et al. | |
| 7,929,537 B2 | 4/2011 | Vasudevan et al. | |
| 7,929,970 B1 | 4/2011 | Gunasekara | |
| 7,941,144 B2 | 5/2011 | Nylander et al. | |
| 7,995,994 B2 * | 8/2011 | Khetawat et al. | 455/410 |
| 8,064,909 B2 | 11/2011 | Spinelli et al. | |
| 8,103,285 B2 | 1/2012 | Kalhan et al. | |
| 8,108,923 B1 | 1/2012 | Satish et al. | |
| 8,437,745 B2 * | 5/2013 | Theppasandra et al. | 455/413 |
| 2002/0044639 A1 | 4/2002 | Shioda et al. | |
| 2002/0077115 A1 | 6/2002 | Ruutu et al. | |
| 2002/0098837 A1 | 7/2002 | Ferrario et al. | |
| 2002/0107018 A1 | 8/2002 | Nakamura et al. | |
| 2002/0123365 A1 | 9/2002 | Thorson | |
| 2002/0142791 A1 | 10/2002 | Chen et al. | |
| 2003/0028621 A1 | 2/2003 | Furlong et al. | |
| 2003/0109271 A1 | 6/2003 | Lewis et al. | |
| 2003/0125044 A1 | 7/2003 | Deloach | |
| 2003/0133558 A1 | 7/2003 | Kung et al. | |
| 2003/0139180 A1 | 7/2003 | McIntosh et al. | |
| 2003/0142637 A1 | 7/2003 | Khawer et al. | |
| 2003/0144793 A1 | 7/2003 | Melaku et al. | |
| 2003/0153302 A1 | 8/2003 | Lewis et al. | |
| 2004/0111382 A1 | 6/2004 | Haji-Ioannou | |
| 2004/0125781 A1 | 7/2004 | Walter et al. | |
| 2004/0203846 A1 | 10/2004 | Caronni et al. | |
| 2004/0235455 A1 | 11/2004 | Jiang | |
| 2004/0236702 A1 | 11/2004 | Fink et al. | |
| 2004/0258003 A1 | 12/2004 | Kokot et al. | |
| 2004/0264428 A1 | 12/2004 | Choi et al. | |
| 2005/0003797 A1 | 1/2005 | Baldwin | |
| 2005/0009499 A1 | 1/2005 | Koster | |
| 2005/0024201 A1 | 2/2005 | Culpepper et al. | |
| 2005/0026650 A1 | 2/2005 | Russell | |
| 2005/0075114 A1 | 4/2005 | Dennison et al. | |
| 2005/0108529 A1 | 5/2005 | Juneau | |
| 2005/0144279 A1 * | 6/2005 | Wexelblat | 709/225 |
| 2005/0160276 A1 | 7/2005 | Braun et al. | |
| 2005/0172148 A1 | 8/2005 | Ying | |
| 2005/0177645 A1 | 8/2005 | Dowling et al. | |
| 2005/0223389 A1 | 10/2005 | Klein et al. | |
| 2005/0239448 A1 | 10/2005 | Bayne | |
| 2005/0250527 A1 | 11/2005 | Jugl | |
| 2005/0254451 A1 | 11/2005 | Grosbach | |
| 2005/0255893 A1 | 11/2005 | Jin et al. | |
| 2005/0259654 A1 | 11/2005 | Faulk, Jr. | |
| 2005/0269402 A1 | 12/2005 | Spitzer et al. | |
| 2005/0283518 A1 | 12/2005 | Sargent | |
| 2006/0031387 A1 | 2/2006 | Hamzeh et al. | |
| 2006/0031493 A1 | 2/2006 | Cugi | |
| 2006/0046647 A1 | 3/2006 | Parikh et al. | |
| 2006/0074814 A1 | 4/2006 | Lovell et al. | |
| 2006/0075098 A1 | 4/2006 | Becker et al. | |
| 2006/0182074 A1 | 8/2006 | Kubler et al. | |
| 2006/0223498 A1 | 10/2006 | Gallagher et al. | |
| 2006/0244589 A1 | 11/2006 | Schranz | |
| 2006/0281457 A1 | 12/2006 | Huotari et al. | |
| 2007/0002844 A1 | 1/2007 | Ali | |
| 2007/0008894 A1 | 1/2007 | Lynch et al. | |
| 2007/0025245 A1 | 2/2007 | Porras et al. | |
| 2007/0032225 A1 | 2/2007 | Konicek et al. | |
| 2007/0032269 A1 | 2/2007 | Shostak | |
| 2007/0066318 A1 * | 3/2007 | Danzeisen et al. | 455/450 |
| 2007/0074272 A1 | 3/2007 | Watanabe | |
| 2007/0094601 A1 | 4/2007 | Greenberg et al. | |
| 2007/0097093 A1 | 5/2007 | Ohshita et al. | |
| 2007/0097938 A1 * | 5/2007 | Nylander et al. | 370/338 |
| 2007/0097939 A1 | 5/2007 | Nylander et al. | |
| 2007/0097983 A1 * | 5/2007 | Nylander et al. | 370/395.2 |
| 2007/0099561 A1 | 5/2007 | Voss | |
| 2007/0104166 A1 * | 5/2007 | Rahman et al. | 370/338 |
| 2007/0111706 A1 | 5/2007 | Kumar et al. | |
| 2007/0123253 A1 | 5/2007 | Simongini et al. | |
| 2007/0124802 A1 * | 5/2007 | Anton et al. | 726/3 |
| 2007/0133563 A1 | 6/2007 | Hundscheidt et al. | |
| 2007/0150732 A1 | 6/2007 | Suzuki et al. | |
| 2007/0155421 A1 | 7/2007 | Alberth et al. | |
| 2007/0167175 A1 | 7/2007 | Wong | |
| 2007/0183427 A1 | 8/2007 | Nylander et al. | |
| 2007/0184815 A1 | 8/2007 | Aebi | |
| 2007/0199076 A1 | 8/2007 | Rensin et al. | |
| 2007/0220252 A1 * | 9/2007 | Sinko | 713/168 |
| 2007/0232332 A1 | 10/2007 | Holur et al. | |
| 2007/0258418 A1 | 11/2007 | Wurtenberger et al. | |
| 2007/0270152 A1 | 11/2007 | Nylander et al. | |
| 2007/0275739 A1 | 11/2007 | Blackburn | |
| 2007/0287501 A1 | 12/2007 | Hoshina | |
| 2008/0043972 A1 | 2/2008 | Ruetschi et al. | |
| 2008/0049702 A1 | 2/2008 | Meylan et al. | |
| 2008/0065752 A1 | 3/2008 | Ch'ng et al. | |
| 2008/0076392 A1 * | 3/2008 | Khetawat et al. | 455/411 |
| 2008/0076393 A1 * | 3/2008 | Khetawat et al. | 455/411 |
| 2008/0076398 A1 | 3/2008 | Mate et al. | |
| 2008/0076412 A1 | 3/2008 | Khetawat et al. | |
| 2008/0076419 A1 | 3/2008 | Khetawat et al. | |
| 2008/0076420 A1 | 3/2008 | Khetawat et al. | |
| 2008/0076425 A1 | 3/2008 | Khetawat et al. | |
| 2008/0081636 A1 * | 4/2008 | Nylander et al. | 455/452.2 |
| 2008/0082538 A1 | 4/2008 | Meijer et al. | |
| 2008/0119160 A1 | 5/2008 | Andriantsiferana et al. | |
| 2008/0126531 A1 | 5/2008 | Setia et al. | |
| 2008/0132239 A1 | 6/2008 | Khetawat et al. | |
| 2008/0133742 A1 | 6/2008 | Southiere et al. | |
| 2008/0141348 A1 | 6/2008 | Hovnanian et al. | |
| 2008/0151807 A1 | 6/2008 | Meier et al. | |
| 2008/0168099 A1 | 7/2008 | Skaf | |
| 2008/0181184 A1 | 7/2008 | Kezys | |
| 2008/0201076 A1 | 8/2008 | Huang et al. | |
| 2008/0207170 A1 * | 8/2008 | Khetawat et al. | 455/411 |
| 2008/0242280 A1 | 10/2008 | Shapiro et al. | |
| 2008/0244148 A1 | 10/2008 | Nix et al. | |
| 2008/0254792 A1 | 10/2008 | Ch'ng | |
| 2008/0261602 A1 | 10/2008 | Livneh et al. | |
| 2008/0274753 A1 | 11/2008 | Attar et al. | |
| 2008/0281687 A1 | 11/2008 | Hurwitz et al. | |
| 2008/0282327 A1 | 11/2008 | Winget et al. | |
| 2008/0299984 A1 | 12/2008 | Shimomura | |
| 2008/0299992 A1 | 12/2008 | Eitan et al. | |

(56) References Cited

U.S. PATENT DOCUMENTS

| | | |
|---|---|---|
| 2008/0305792 A1 | 12/2008 | Khetawat et al. |
| 2008/0305801 A1 | 12/2008 | Burgess et al. |
| 2008/0305834 A1 | 12/2008 | Janiszewski et al. |
| 2008/0318551 A1 | 12/2008 | Palamara et al. |
| 2009/0012898 A1 | 1/2009 | Sharma et al. |
| 2009/0031006 A1 | 1/2009 | Johnson et al. |
| 2009/0037973 A1 | 2/2009 | Gustave et al. |
| 2009/0042593 A1 | 2/2009 | Yavuz et al. |
| 2009/0046665 A1 | 2/2009 | Robson et al. |
| 2009/0047945 A1 | 2/2009 | Zhang |
| 2009/0059822 A1 | 3/2009 | Morrill et al. |
| 2009/0061821 A1 | 3/2009 | Chen et al. |
| 2009/0061873 A1 | 3/2009 | Bao et al. |
| 2009/0077620 A1 * | 3/2009 | Ravi et al. ............ 726/1 |
| 2009/0082010 A1 | 3/2009 | Lee |
| 2009/0082020 A1 | 3/2009 | Ch'ng et al. |
| 2009/0092080 A1 * | 4/2009 | Balasubramanian et al. 370/328 |
| 2009/0092081 A1 * | 4/2009 | Balasubramanian et al. 370/328 |
| 2009/0092096 A1 | 4/2009 | Czaja |
| 2009/0092097 A1 * | 4/2009 | Nylander et al. ............ 370/331 |
| 2009/0093232 A1 * | 4/2009 | Gupta et al. .............. 455/410 |
| 2009/0094351 A1 * | 4/2009 | Gupta et al. .............. 709/220 |
| 2009/0094680 A1 * | 4/2009 | Gupta et al. .............. 726/3 |
| 2009/0097436 A1 | 4/2009 | Vasudevan et al. |
| 2009/0098871 A1 * | 4/2009 | Gogic ............. 455/435.1 |
| 2009/0111499 A1 | 4/2009 | Bosch |
| 2009/0122773 A1 | 5/2009 | Gogic |
| 2009/0124262 A1 | 5/2009 | Vela et al. |
| 2009/0129336 A1 | 5/2009 | Osborn et al. |
| 2009/0129350 A1 * | 5/2009 | Khandekar et al. ........... 370/338 |
| 2009/0131050 A1 | 5/2009 | Osborn |
| 2009/0131098 A1 * | 5/2009 | Khandekar et al. ........... 455/525 |
| 2009/0135749 A1 | 5/2009 | Yang |
| 2009/0135794 A1 | 5/2009 | Su et al. |
| 2009/0156213 A1 | 6/2009 | Spinelli et al. |
| 2009/0161682 A1 | 6/2009 | Johnson et al. |
| 2009/0163216 A1 | 6/2009 | Hoang et al. |
| 2009/0163224 A1 | 6/2009 | Dean |
| 2009/0164547 A1 * | 6/2009 | Ch'ng et al. .............. 709/201 |
| 2009/0170440 A1 | 7/2009 | Eyuboglu et al. |
| 2009/0170528 A1 | 7/2009 | Bull et al. |
| 2009/0180428 A1 | 7/2009 | Viswanath |
| 2009/0191844 A1 * | 7/2009 | Morgan et al. .............. 455/411 |
| 2009/0191845 A1 * | 7/2009 | Morgan et al. .............. 455/411 |
| 2009/0210324 A1 * | 8/2009 | Bhogal et al. .............. 705/28 |
| 2009/0213825 A1 | 8/2009 | Gupta et al. |
| 2009/0215429 A1 | 8/2009 | Caldwell et al. |
| 2009/0215452 A1 | 8/2009 | Balasubramanian et al. |
| 2009/0221303 A1 | 9/2009 | Soliman |
| 2009/0233574 A1 | 9/2009 | Shinozaki |
| 2009/0245176 A1 | 10/2009 | Balasubramanian et al. |
| 2009/0253421 A1 | 10/2009 | Camp et al. |
| 2009/0253432 A1 | 10/2009 | Willey et al. |
| 2009/0257434 A1 | 10/2009 | Song et al. |
| 2009/0279701 A1 | 11/2009 | Moisand et al. |
| 2009/0291667 A1 | 11/2009 | Vakil et al. |
| 2009/0325634 A1 | 12/2009 | Bienas et al. |
| 2010/0022266 A1 | 1/2010 | Villier |
| 2010/0040026 A1 | 2/2010 | Melkesetian |
| 2010/0048165 A1 | 2/2010 | Caldwell et al. |
| 2010/0113067 A1 | 5/2010 | Fullam et al. |
| 2010/0167777 A1 | 7/2010 | Raghothaman et al. |
| 2010/0260068 A1 | 10/2010 | Bhatt et al. |
| 2011/0177794 A1 * | 7/2011 | Nylander et al. ............. 455/411 |
| 2011/0200022 A1 | 8/2011 | Annamalai |
| 2011/0280154 A1 | 11/2011 | Silverstrim et al. |

FOREIGN PATENT DOCUMENTS

| | | |
|---|---|---|
| EP | 2252122 A1 * | 11/2010 |
| GB | 2425291 A | 10/2006 |
| GB | 2425921 A | 11/2006 |
| JP | 20010264096 | 9/2001 |
| JP | 2003022303 | 1/2003 |
| JP | 2003288521 | 10/2003 |
| JP | 2004112324 | 4/2004 |
| JP | 2005073147 | 3/2005 |
| JP | 2005215849 | 8/2005 |
| JP | 2006067143 | 3/2006 |
| JP | 2008048055 | 2/2008 |
| WO | 0214987 | 2/2002 |
| WO | 2005076964 A2 | 8/2005 |
| WO | 2007015067 A2 | 2/2007 |
| WO | 2007040449 A1 | 4/2007 |
| WO | 2008047039 A1 | 4/2008 |

OTHER PUBLICATIONS

International Search Report and Written Opinion mailed Feb. 23, 2010, for PCT Application No. PCT/US2009/043846, 13 pages.
OA dated Dec. 31, 2009 for U.S. Appl. No. 11/457,129, 16 pages.
OA dated Apr. 17, 2009 for U.S. Appl. No. 11/276,269, 15 pages.
OA dated Nov. 4, 2008 for U.S. Appl. No. 11/276,269, 15 pages.
OA dated Jun. 17, 2010 for U.S. Appl. No. 11/457,129, 15 pages.
Kaul, "Verizon's $250 femto box—A deliberate ploy behind the aggressive pricing?" Posted Tue, Jan. 20, 2009 13:19:46 EST; http://www.abiresearch.com/research_blog/569; © 2009 Allied Business Intelligence, Inc.
International Search Report and Written Opinion dated Oct. 27, 2009 for PCT Application Serial No. PCT/US2009/043861, 14 Pages.
OA dated Jun. 22, 2011 for U.S. Appl. No. 12/484,072, 38 pages.
OA dated Jul. 7, 2011 for U.S. Appl. No. 12/276,257, 24 pages.
OA dated Jun. 28, 2011 for U.S. Appl. No. 12/275,925, 18 pages.
OA dated Jun. 8, 2011 for U.S. Appl. No. 12/484,026, 30 pages.
OA dated Mar. 29, 2011 for U.S. Appl. No. 12/276,002, 37 pages.
OA dated Apr. 13, 2011 for U.S. Appl. No. 12/276,058, 40 pages.
OA dated Apr. 19, 2011 for U.S. Appl. No. 12/276,238, 22 pages.
OA dated May 5, 2011 for U.S. Appl. No. 12/275,015, 32 pages.
OA dated Aug. 18, 2011 for U.S. Appl. No. 12/275,416, 39 pages.
OA dated Sep. 14, 2011 for U.S. Appl. No. 12/276,002, 35 pages.
OA dated Oct. 5, 2011 for U.S. Appl. No. 12/276,058, 37 pages.
OA dated Oct. 6, 2011 for U.S. Appl. No. 12/465,483, 50 pages.
OA dated Oct. 4, 2011 for U.S. Appl. No. 12/484,135, 44 pages.
OA dated Jul. 21, 2011 for U.S. Appl. No. 12/175,293, 30 pages.
OA dated Mar. 5, 2012 for U.S. Appl. No. 12/465,598, 55 pages.
OA dated Mar. 19, 2012 for U.S. Appl. No. 12/276,120, 68 pages.
OA dated Mar. 30, 2012 for U.S. Appl. No. 12/484,026, 30 pages.
Notice of Allowance dated Apr. 3, 2012 for U.S. Appl. No. 12/275,996, 38 pages.
OA dated Apr. 10, 2012 for U.S. Appl. No. 12/275,416, 32 pages.
OA dated Apr. 10, 2012 for U.S. Appl. No. 12/484,135, 45 pages.
OA dated Apr. 13, 2012 for U.S. Appl. No. 13/316,106, 35 pages.
Notice of Allowance dated Apr. 25, 2012 for U.S. Appl. No. 12/465,468, 35 pages.
OA dated May 8, 2012 for U.S. Appl. No. 11/457,129, 38 pages.
OA dated Oct. 24, 2011 for U.S. Appl. No. 12/275,925, 14 pages.
OA dated Jan. 5, 2012 for U.S. Appl. No. 12/465,585, 43 pages.
OA dated Dec. 1, 2011 for U.S. Appl. No. 12/275,996, 44 pages.
OA dated Oct. 25, 2011 for U.S. Appl. No. 12/465,580, 39 pages.
OA dated Nov. 8, 2011 for U.S. Appl. No. 12/465,468, 50 pages.
OA dated Dec. 28, 2011 for U.S. Appl. No. 12/175,293, 38 pages.
OA dated Nov. 21, 2011 for U.S. Appl. No. 12/484,026, 37 pages.
OA dated Dec. 14, 2011 for U.S. Appl. No. 12/484,072, 44 pages.
OA dated Nov. 1, 2011 for U.S. Appl. No. 12/816,087, 33 pages.
OA dated Sep. 10, 2012 for U.S. Appl. No. 12/276,002, 54 pages.
OA dated Jul. 10, 2012 for U.S. Appl. No. 12/465,585, 32 pages.
OA dated Sep. 5, 2012 for U.S. Appl. No. 12/276,120, 49 pages.
OA dated Aug. 16, 2012 for U.S. Appl. No. 12/465,598, 31 pages.
OA dated Sep. 6, 2012 for U.S. Appl. No. 12/579,957, 51 pages.
Office Action dated Apr. 23, 2013 for U.S. Appl. No. 12/175,293, 41 pages.
Canadian Office Action mailed Mar. 26, 2013 for Canadian Patent Application No. 2,722,324, 4 pages.
Office Action dated Jul. 15, 2013 for U.S. Appl. No. 13/554,710, 37 pages.
Office Action dated Jan. 17, 2013 for U.S. Appl. No. 13/554,710, 42 pages.
Final OA dated Feb. 15, 2013 for U.S. Appl. No. 12/579,957.

(56) References Cited

OTHER PUBLICATIONS

OA dated Feb. 26, 2013 for U.S. Appl. No. 12/276,120, 59 pages.
Chinese Office Action for Chinese Application No. 200980117263.8 dated Feb. 16, 2013, 7 pages.
Chinese Office Action for Chinese Application No. 200980117188.5 dated Jan. 31, 2013, 11 pages.
Final OA dated Mar. 14, 2013 for U.S. Appl. No. 12/484,072, 34 pages.
OA dated Oct. 2, 2012 for U.S. Appl. No. 12/484,026, 29 pages.
OA dated Oct. 11, 2012 for U.S. Appl. No. 13/487,794, 45 pages.
OA dated Oct. 9, 2012 for U.S. Appl. No. 13/298,924, 51 pages.
OA dated Nov. 1, 2012 for U.S. Appl. No. 12/276,058, 59 pages.
Oa dated Nov. 5, 2012 for U.S. Appl. No. 12/484,072, 52 pages.
Japanese Office Action mailed Sep. 13, 2012 for Japanese Patent Application No. 2011-509669, 10 pages.
Canadian Office Action mailed Oct. 30, 2012 for Canadian Patent Application No. 2,722,324, 3 pages.
Japanese Office Action mailed Sep. 13, 2012 for Japanese Patent Application No. 2011-509675, 4 pages.
Office Action dated Dec. 3, 2012 for U.S. Appl. No. 12/275,416, 33 pages.
Office Action dated Aug. 13, 2013 for U.S. Appl. No. 12/276,120, 66 pages.
Office Action dated Aug. 12, 2013 for U.S. Appl. No. 12/275,416, 36 pages.
Office Action dated Oct. 2, 2013 for U.S. Appl. No. 12/275,878, 38 pages.
Office Action dated Oct. 22, 2013 for U.S. Appl. No. 13/898,910, 50 pages.
Office Action dated Oct. 3, 2013 for U.S. Appl. No. 13/934,644, 17 pages.
Chinese Office Action dated Oct. 24, 2013 for Chinese Patent Application No. 200980117263.8, 13 pages.
Chinese Office Action dated Oct. 21, 2013 for Chinese Patent Application No. 200980117188.5, 11 pages.
Japanese Office Action dated Oct. 3, 2013 for Japanese Patent Application No. 2011-509669, 15 pages.
Office Action dated Sep. 9, 2013 for U.S. Appl. No. 12/465,585, 45 pages.
Office Action dated Dec. 12, 2013 for U.S. Appl. No. 12/276,120, 78 pages.
Japanese Office Action dated Jan. 16, 2014 for Japanese Patent Application No. 2013-026198, 8 pages.
Office Action dated Mar. 26, 2014 for U.S. Appl. No. 12/465,585, 44 pages.
Office Action dated Mar. 24, 2014 for U.S. Appl. No. 13/934,644, 50 pages.
Notice of Allowance dated Apr. 4, 2014 for U.S. Appl. No. 14/090,802, 63 pages.
Office Action dated Mar. 24, 2014 for U.S. Appl. No. 13/671,191, 63 pages.

* cited by examiner

INTERACTIVE CLIENT MANAGEMENT OF AN ACCESS CONTROL LIST

CROSS-REFERENCE TO RELATED APPLICATION

This application claims the benefit of U.S. Provisional Patent application Ser. No. 61/052,813 entitled "MANAGEMENT OF ACCESS TO FEMTO CELL COVERAGE" and filed on May 13, 2008. The entirety of the above-referenced application is incorporated by reference herein.

TECHNICAL FIELD

The subject innovation generally relates to wireless communications, and, more particularly, to interactive client management of an access control list associated with a femtocell.

BACKGROUND

Femtocells—building-based wireless access points interfaced with a wired broadband network—are generally deployed to improve indoor wireless coverage provided by a wireless network operator. Femtocells typically operate in licensed portions of the electromagnetic spectrum, and generally offer plug-and-play installation; e.g., automatic configuration of femto access point. Improved indoor coverage includes stronger signal and improved reception (e.g., voice or sound), ease of session or call initiation and session or call retention as well. Coverage of a femtocell, or femto AP, is intended to be confined within the bounds of an indoor compound, in order to mitigate interference among mobile stations covered by a macro cell and terminals covered by the femto AP. Additionally, confined coverage can reduce crosstalk among terminals serviced by disparate, neighboring femtocells as well.

Coverage improvements via femtocells also can mitigate customer attrition as long as a favorable subscriber perception regarding voice coverage and other data services with substantive delay sensitivity is attained. A positive customer experience can depend on adequate access management to femtocell service.

It can be desirable to encourage communication devices to utilize a femtocell owned/operated by a subscriber and services available via the femtocell, as it can facilitate communication of information between communication devices and respective users of those communication devices and/or can generate income for the subscriber that owns/operates the femtocell. It also can be desirable to manage access of wireless communication devices to a femtocell to facilitate efficient use of bandwidth and services associated with the femtocell. It also can be desirable to manage access of wireless communication devices to a femtocell in order to facilitate reducing unnecessary signaling between a femtocell and a communication device(s) in the coverage area of the femtocell, where the communication device(s) is not desiring or is not authorized to access the femtocell.

SUMMARY

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The subject innovation provides system(s) and method(s) to manage access to femtocell service through access control list(s), or "white list(s)." In an aspect, the white list(s) can be configured via a networked interface that can facilitate access management to a femtocell. A white list(s) can include a set of subscriber station(s) identifier numbers, codes or tokens, and can also include additional fields that can facilitate femtocell access management based at least in part on desired complexity.

In an aspect, the femtocell can facilitate automatically querying a subscriber station(s) (e.g., cellular phone, computer, . . . ), which is detected in a femtocell coverage area of the femtocell, to prompt the subscriber station(s) to access or request access to the femtocell and services associated therewith to facilitate populating the white list with desired subscriber stations. In an aspect, the femtocell (e.g., femto access point) can detect a subscriber station(s) that has entered a femtocell coverage area of the femtocell. The femtocell can include an access management component that can facilitate managing access to femtocell coverage and services associated therewith. The access management component can automatically generate and transmit a query to a detected subscriber station to prompt the subscriber station to access or request to access the femtocell and associated services and to be entered on the white list(s) of the femtocell. In response to the query, the subscriber station can opt in to access the femtocell and associated services, or subset thereof, and to be entered on the white list(s) on a permanent basis or temporary basis, or can opt out of accessing the femtocell and associated services.

The access management component can determine whether to grant access to the femtocell and an associated subset of services (e.g., voice service(s), data service(s), access or download content, etc.), on a temporary or permanent basis, based at least in part on slot availability of the femtocell (and white list) and other predefined access criteria, and/or a request (e.g., request to opt in to access the femtocell on a temporary basis, request to opt in to access the femtocell on a permanent basis) received from the subscriber station. The access management component can store information related to the subscriber station in the white list on a permanent or temporary basis, when the subscriber station is granted access to the femtocell and the subset of services. When granted access to the femtocell and subset of services, the subscriber station can communicate with other subscriber stations and/or can access and utilize the subset of services provided via the femtocell. When information related to the subscriber station is stored in the white list on a temporary basis, the information related to the subscriber station can be deleted from the white list when a predefined period of time (or an extension to the predefined period of time) is expired or the subscriber station is no longer detected by the femtocell (e.g., subscriber station leaves the femtocell coverage area, subscriber station is powered down). Access to the femtocell and the associated subset of services by the subscriber station can be terminated when the grant of access has expired (e.g., when granted on a temporary basis) and/or the subscriber station has left the femtocell coverage area or is powered down.

The access management component can determine whether to deny access to a femtocell and an associated subset of services on a temporary or permanent basis, based at least in part on predefined access criteria and/or a request (e.g., request to opt out of access the femtocell on a temporary basis, request to opt out of access the femtocell on a permanent basis) received from the subscriber station. The access management component can store information related to the subscriber station in a black list associated with the femtocell on a permanent or temporary basis, when the subscriber station is denied access (or refuses access) to the femtocell and the subset of services, based at least in part on the predefined access criteria or the request (e.g., request to opt out of access the femtocell on a temporary basis, request to opt out of access the femtocell on a permanent basis) received from the subscriber station. When information related to the subscriber station is stored in the black list on a temporary basis, the information related to the subscriber station can be deleted from the black list when a predefined period of time is expired or the subscriber station is no longer detected by the femtocell (e.g., subscriber station leaves the femtocell coverage area, subscriber station is powered down).

To the accomplishment of the foregoing and related ends, the invention, then, comprises the features hereinafter fully described. The following description and the annexed drawings set forth in detail certain illustrative aspects of the invention. However, these aspects are indicative of but a few of the various ways in which the principles of the invention may be employed. Other aspects, advantages and novel features of the invention will become apparent from the following detailed description of the invention when considered in conjunction with the drawings.

DETAILED DESCRIPTION

Figure 1:
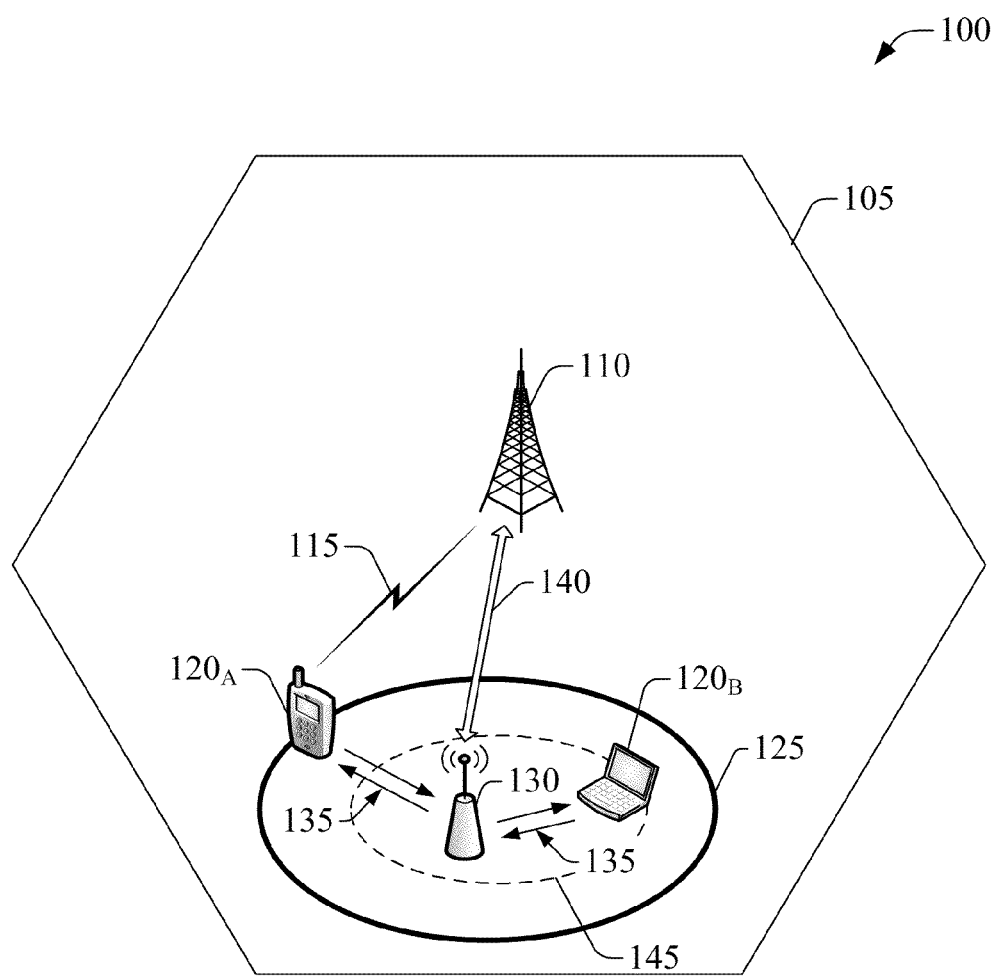
FIG. 1 a schematic deployment of a macro cell and a femtocell for wireless coverage in accordance with aspects described herein.

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

As used in this application, the terms "component," "system," "platform," and the like can refer to a computer-related entity or an entity related to an operational machine with one or more specific functionalities. The entities disclosed herein can be either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers. Also, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal).

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

Moreover, terms like "user equipment," "mobile station," "mobile," "subscriber station," "communication device," "access terminal," "terminal," "handset," and similar terminology, refer to a wireless device utilized by a subscriber or user of a wireless communication service to receive or convey data, control, voice, video, sound, gaming, or substantially any data-stream or signaling-stream. The foregoing terms are utilized interchangeably in the subject specification and related drawings. Likewise, the terms "access point," "base station," "Node B," "evolved Node B," "home Node B (HNB)," and the like, are utilized interchangeably in the subject application, and refer to a wireless network component or appliance that serves and receives data, control, voice, video, sound, gaming, or substantially any data-stream or signaling-stream from a set of subscriber stations. Data and signaling streams can be packetized or frame-based flows.

Furthermore, the terms "user," "subscriber," "customer," "consumer," "prosumer," "agent," and the like are employed interchangeably throughout the subject specification, unless context warrants particular distinction(s) among the terms. As utilized herein, the term "prosumer" indicate the following contractions: professional-consumer and producer-consumer.

The following abbreviations are relevant to the subject specification.

3G Third Generation
3GPP Third Generation Partnership Project
AGPS Assisted GPS
AP Access Point
ADSL Asymmetric Digital Subscriber Line
AWS Advanced Wireless Services
BRAS Broadband Remote Access Server
BTA Basic Trading Area
CN Core Network
CS Circuit-Switched
CSCF Call Session Control Function
CPE Customer Premise Equipment
CPN Customer Premise Network
DHCP Dynamic Host Configuration Protocol
DSL Digital Subscriber Line
DSLAM Digital Subscriber Line Access Multiplexer
E911 Enhanced 911
FCC Federal Communications Commission
FL Forward Link
GGSN Gateway GPRS Service Node
GPRS General Packet Radio Service
GPS Global Positioning System
GW Gateway
HAP Home Access Point
HSS Home Subscriber Server
ISDN Integrated Services Digital Network
UE User Equipment
UTRAN Universal Terrestrial Radio Access Network
IMS IP Multimedia Subsystem
IP Internet Protocol
ISP Internet Service Provider
MSA Metropolitan Statistical Areas
MSISDN Mobile Subscriber ISDN Number
MTA Major Trading Areas
NAT Network Address Translation
NTP Network Time Protocol
O&M Operation and Maintenance
PC Personal Computer
PCS Personal Communications Service
PS Packet-Switched
PSTN Public Switched Telephone Network
RAN Radio Access Network
RBS Radio Base Station
RL Reverse Link
RNC Radio Network Controller
RSA Rural Service Area
SGSN Serving GPRS Support Node
SIP Session Initiation Protocol
USSD Unstructured Supplementary Service Data
VPN Virtual Private Network
WAP Wireless Application Protocol
XDSL Asynchronous-DSL or Synchronous-DSL Referring to the drawings, FIG. 1 illustrates a schematic wireless environment 100 (e.g., a network) in which a femtocell can exploit various aspects of the subject innovation in accordance with the disclosed subject matter. In wireless environment 100, area 105 can represent a coverage macro cell which can be served by base station 110. Macro coverage is generally intended for outdoors locations for servicing mobile wireless devices, like UE $120_A$, and such coverage is achieved via a wireless link 115. In an aspect, UE $120_A$ can be a 3GPP Universal Mobile Telecommunication System (UMTS) mobile phone.

Within macro coverage cell 105, a femtocell 145, served by a femto access point 130, can be deployed. A femtocell typically can cover an area 125 that is determined, at least in part, by transmission power allocated to femto AP 130, path loss, shadowing, and so forth. Coverage area typically can be spanned by a coverage radius that ranges from 20 to 50 meters. Confined coverage area 145 is generally associated with an indoors area, or a building, which can span about 5000 sq. ft. Generally, femto AP 130 typically can service a number (e.g., a few or more) wireless devices (e.g., subscriber station $120_B$) within confined coverage area 145. In an aspect, femto AP 130 can integrate seamlessly with substantially any PS-based and CS-based network; for instance, femto AP 130 can integrate into an existing 3GPP Core via conventional interfaces like Iu-CS, Iu-PS, Gi, Gn. In another aspect, femto AP 130 can exploit high-speed downlink packet access in order to accomplish substantive bitrates. In yet another aspect, femto AP 130 has a LAC (location area code) and RAC (routing area code) that can be different than the underlying macro network. These LAC and RAC are used to identify subscriber station location for a variety of reasons, most notably to direct incoming voice and data traffic to appropriate paging transmitters.

As a subscriber station, e.g., UE $120_A$, leaves macro coverage (e.g., cell 105) and enters femto coverage (e.g., area 125), as illustrated in environment 100, UE $120_A$ can attempt to attach to the femto AP 130 through transmission and reception of attachment signaling, effected via a FL/RL 135; in an aspect, the attachment signaling can include a Location Area Update (LAU) and/or Routing Area Update (RAU). Attachment attempts are a part of procedures to ensure mobility, so voice calls and sessions can continue even after a macro-to-femto transition or vice versa. It is to be noted that the subscriber station (e.g., UE $120_A$) can be employed seamlessly after either of the foregoing transitions. Femto networks are also designed to serve stationary or slow-moving traffic with reduced signaling loads compared to macro networks. A femto service provider (e.g., an entity that commercializes, deploys, and/or utilizes femto access point 130) therefore can be inclined to minimize unnecessary LAU/RAU signaling activity at substantially any opportunity to do so, and through substantially any available means. It is to be noted that substantially any mitigation of unnecessary attachment signaling/control can be advantageous for femtocell operation. Conversely, if not successful, UE $120_A$ generally can be commanded (through a variety of communication means) to select another LAC/RAC or enter "emergency calls only" mode. It is to be appreciated that this attempt and handling process can occupy significant UE battery, and femto AP capacity and signaling resources as well.

When an attachment attempt is successful, UE $120_A$ can be allowed on femtocell 125 and incoming voice and data traffic can be paged and routed to the subscriber station through the femto AP 130. It is to be noted also that data traffic is typically routed through a backhaul broadband wired network backbone 140 (e.g., optical fiber backbone, twisted-pair line, T1/E1 phone line, DSL, or coaxial cable). To this end, femto AP 130 can be connected to the broadband backhaul network backbone 140 via a broadband modem (not shown).

It is to be noted that as a femto AP 130 generally can rely on a backhaul network backbone 140 for routing and paging, and for packet communication, substantially any quality of service can handle heterogeneous packetized traffic. Namely, packet flows established for wireless communication devices (e.g., terminals $120_A$ and $120_B$) served by femto AP 130, and for devices served through the backhaul network pipe 140. It is to be noted that to ensure a positive subscriber experience, or perception, it is desirable for femto AP 130 to maintain a high level of throughput for traffic (e.g., voice and data) utilized on a mobile device for one or more subscribers while in the presence of external, additional packetized, or broadband, traffic associated with applications (e.g., web browsing, data transfer (e.g., content upload), and the like) executed in devices within the femto coverage area (e.g., area 125 or area 145).

Figure 2:
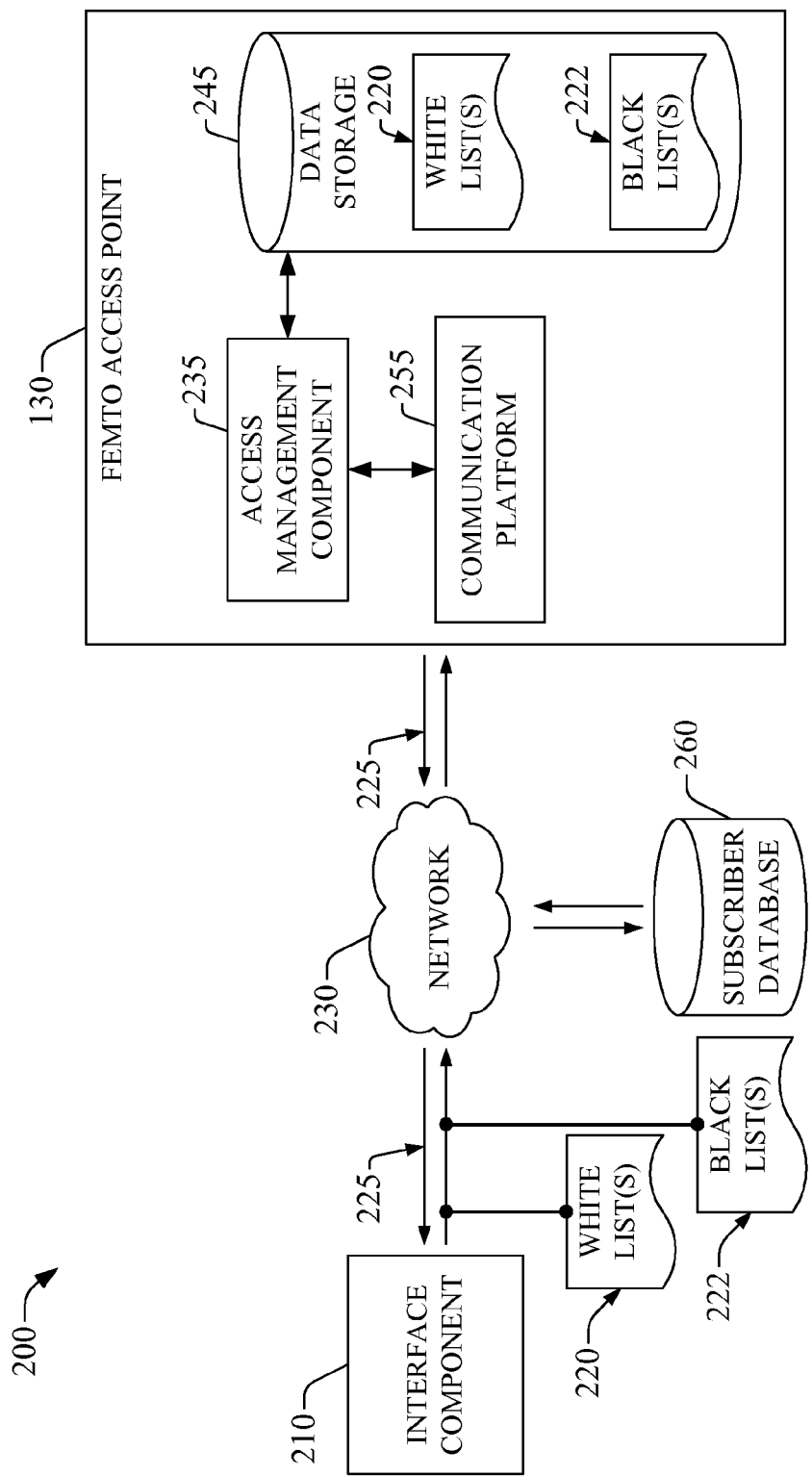
FIG. 2 is a block diagram of an example system that can facilitate selection of subscribers and/or subscriber stations to access coverage from a femtocell in accordance with an embodiment of the disclosed subject matter.

FIG. 2 is a block diagram of an example system 200 that can facilitate selection of subscribers and/or subscriber stations to access coverage from a femtocell in accordance with an embodiment of the disclosed subject matter. In an aspect, selection of subscribers and/or subscriber stations can enable or disable femtocell coverage for specific subscriber(s) or subscriber station(s). A means provided by example system 200 to facilitate authorizing, denying, revoking, and/or terminating access to specific subscribers, or subscriber station(s), comprises what is herein termed as a "White List(s)" (e.g., access control list(s))—an instrument that can facilitate management of access to femtocell coverage.

In example system 200, an interface component 210 can facilitate configuration, or set up, of a list(s) (e.g., white list 220, black list 222) of wireless mobile station numbers approved for coverage through femto access point 130. It is to be noted that substantially any identification token(s), label(s), or code(s) that can facilitate identifying a subscriber station can be employed to identify a subscriber station in a white list 220 or black list 222. In an aspect, a white list(s) 220 associated with femto AP 130 can include information related to subscriber stations and respectively associated subscribers that are granted respective levels of access to the femto AP 130 on a permanent or temporary basis. In another aspect, a black list(s) 222 associated with femto AP 130 can include information related to subscriber stations and respectively associated subscribers that are not granted access to the femto AP 130, where the opting out (e.g., refusal) or denial of coverage by the femto AP 130 can result in such subscriber stations being included on the black list(s) on a permanent or temporary basis.

In an aspect, the interface 210 can be networked (e.g., via a WAN, LAN, or backhaul pipe) with femto AP 130 and can convey white list(s) 220 and/or black list(s) 222 over network link(s) 225. In an aspect, interface component 210 can be a web-based, online graphic user interface (GUI), and/or other networked interfaces, which can facilitate entering or configuring a white list 220 or black list 222, can be employed, as desired, such as, for example, voice or sound commanded interface(s), touch commanded interface(s), biometric commanded interfaces(s), and the like. A communication platform 255 can facilitate reception of the white list(s) 220 and/or black list(s) 222 and can convey white list(s) 220 and/or black list(s) 222 to an access management component 235 that can exploit the white list(s) 220 and/or black list(s) 222 to facilitate managing access to coverage provided by femto AP 130 to subscriber stations and associated subscribers. White list(s) 220 and/or black list(s) 222 can be stored in the data storage 245 in the femto AP 130; and, as desired, white list(s) 220 and/or black list(s) 222 can be stored in disparate network components such as network component administered by a service operator. In addition, interface component 210 can access a subscriber database through network 230, in order to extract identification numbers, codes, tokens, or labels for subscribers/subscriber stations that can be entered in a white list 220 and/or black list 222.

In an illustrative, not-limiting aspect of the subject innovation, white list(s) 220 (or any set of numbers, codes or tokens thereon, that can comprise a set of subscriber stations (e.g., mobile phones) approved for coverage by femto AP 130) and/or black list(s) 222 (or any set of numbers, codes or tokens thereon, that can comprise a set of subscriber stations (e.g., mobile phones) not approved for coverage by femto AP 130) can be portable through accounts or billing groups associated with a set of subscribers to a service operator that can administer femto AP 130, or a macro network. As an illustration, white list(s) 220 and/or black list(s) 222 each can support up to N fields (N a positive integer; e.g., N=50) for unique mobile phone numbers (e.g., MSIDSNs), or any suitable identifying codes or tokens. The number N of fields can be determined, or configured, by a service operator based at least in part on technical aspects (e.g., network resources, quality of service consideration, macro area of coverage (e.g., MSA/RSA, . . . ) and commercial aspects (e.g., promotional considerations, mitigation of customer attrition, gains in market share, etc.) aspects of provision of coverage. As an example, N can be subscriber dependent or femto AP dependent.

In contrast to management of access authorization via femto AP 130, it should be appreciated that configuration of white list(s) 220 (e.g., registration authorization for femto coverage) and/or black list(s) 222 through a network mechanism(s) (e.g., interface component 210) can provide at least the following advantages. It is to be noted that the following advantages are illustrative and not limiting, as other advantages associated with white list(s) 220 and/or black list(s)

222, as are realized, are intended to lay within the scope of the innovation(s) described in the subject specification. (1) Access through a networked interface (e.g., online or otherwise) can reduce provisioning lead time and provides a means for customers to update and personalize a femto AP autonomously (e.g., free of interaction with technical support entities) at substantially any time. (2) Security against devices attempting to hack into the femto AP when networked with it, and support of extensible sharing/networking of the authorization scheme. (3) Networked interface (e.g., online or otherwise) can provide a superior, rich customer experience substantially free of requirement(s) to understand/interpret femto AP programming interface or configuration nomenclature. (4) End user(s) can manage (e.g., remove select covered numbers, or add additional numbers for coverage up to an allotted amount for white list(s) associated with the user. (5) Capacity to determined Quality of Service (QoS), grade of service, or service experience, for specific authorized subscribers. (6) Capacity to check for valid wireless device numbers, codes or tokens (e.g., MSISDNs); subscriber's active numbers, codes or tokens; and numbers, codes or tokens on service accounts in good standing; such capacity can be provided through networked access to a subscriber database 260.

White list(s) 220 and black list(s) 222 can facilitate management of access to coverage by a femto AP (e.g., femto AP 130) and services associated with the femto AP. Various illustrative aspects of innovation based at least in part on a white list concept also are discussed herein. It is to be noted, notwithstanding, that variations and extensions of such illustrative aspects can be realized and are within the scope of the subject innovation.

Figure 3:
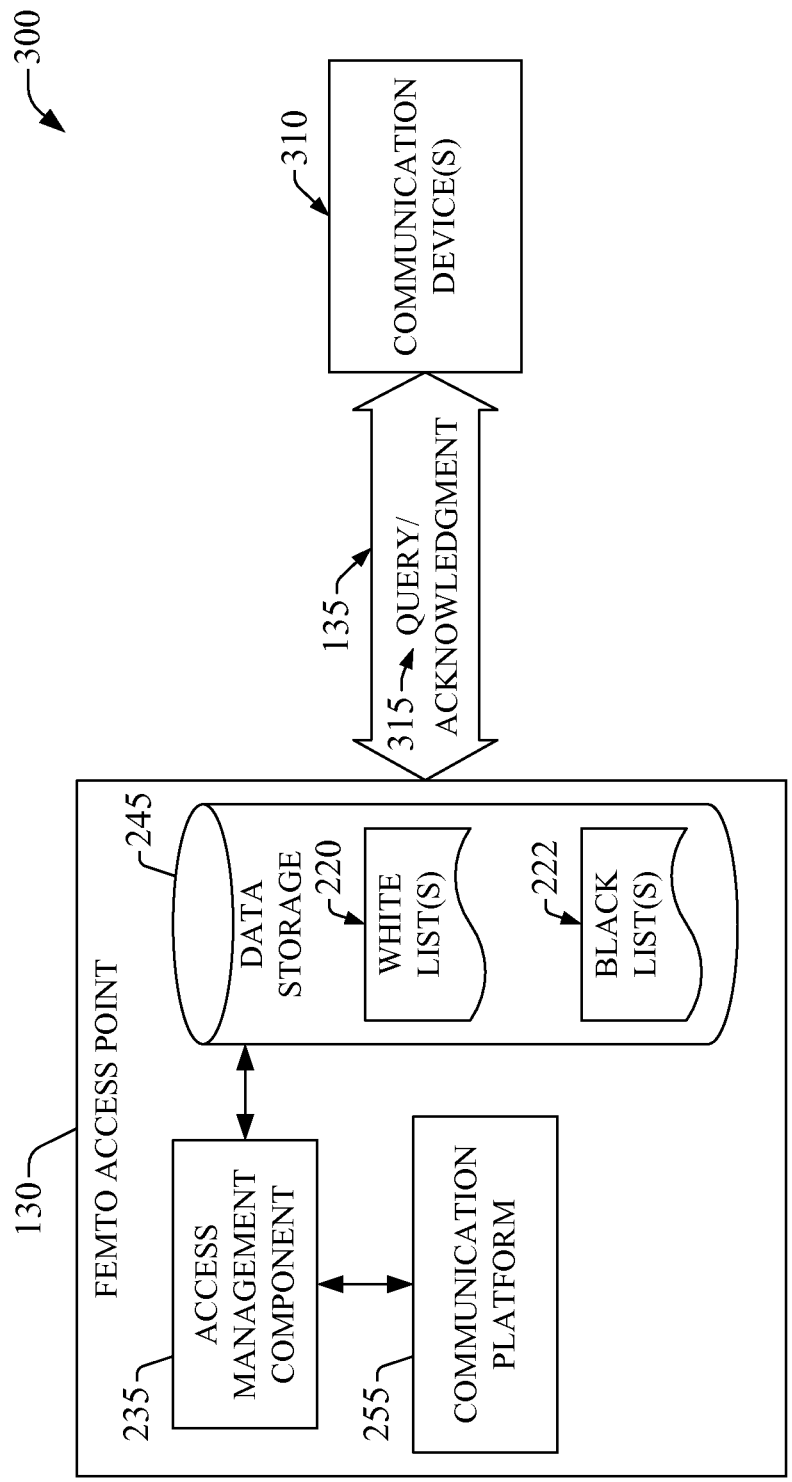
FIG. 3 is a block diagram of an example system that can interactively prompt communication devices to facilitate automatically populating a white list(s) associated with a femto AP and management of access of communication devices to a femto AP in accordance with an aspect of the disclosed subject matter.

FIG. 3 is a block diagram of an example system 300 that can interactively prompt communication devices to facilitate automatically populating a white list(s) associated with a femto AP and management of access of communication devices to a femto AP in accordance with an aspect of the disclosed subject matter. In example system 300, the femto AP 130 can scan a frequency spectrum or band in which communication devices can communicate to facilitate detecting communication devices that are in the cell coverage area (e.g., area 125) of the femto AP 130. The femto AP 130 can automatically detect a communication device(s) 310 (e.g., subscriber station(s), such as a mobile phone (e.g., UE 120$_A$), computer that can communicate in a wireless environment (e.g., subscriber station 120$_B$), or other wireless mobile communication device) that enters the cell coverage area of the femto AP 130. In an aspect, the access management component 235 can facilitate automatically generating and transmitting a query 315, which can be transmitted by the communication platform 255, to the communication device(s) 310 via FL/RL 135 to inquire as to whether the communication device(s) 310 desires to connect (e.g., wirelessly connect) to the femto AP 130 to access services associated with the femto AP 130 and be entered on a white list(s) 220 associated with the femto AP 130. Interactively prompting detected communication devices 310 to opt in to the white list(s) 220 of the femto AP 130 and accessing services associated with the femto AP 130 can facilitate automatically populating the white list(s) 220. The communication device(s) 310 can communicate a response to the prompt or query 315 to accept the invitation to opt in to the white list(s) 220 and request access to the femto AP 130 or can reject the prompt. In another aspect, a communication device(s) 310 can enter the cell coverage area of the femto AP 130 and can convey a request or query 315 to facilitate accessing coverage of femto AP 130. Such a query 315 or request can be received by communication platform 255 via a FL/RL 135. In an aspect, the query 315 can be conveyed via an online GUI, an email message, a SMS message, MMS message, a voice mail, a web prompt, USSD (or * and # codes), and the like.

In another aspect, the access management component 235 can be configured to allow or reject the request for access by the communication device(s) 310, where allowance or rejection of a request can be based at least in part on various metrics (e.g., predefined access criteria), such as security, type of communication device, profile of subscriber that operates/operated the communication device 310 that requests access, historical information regarding the communication device or associated user (e.g., abusive use of the femto AP 130 and associated services), available bandwidth, bandwidth requirements of the communication device, etc. Upon allowance of a request, the access management component 235 can query for available slots to be filled in white list(s) 220 associated with accounts served by femto AP 130, and when space is available in the white list(s) 220 for a subscriber station identifier number (e.g., MSISDN), code or token, and/or other information, the query can further probe whether access is allowed on a permanent or temporary basis (e.g., to reduce risk exposure to security problems, maintain available space on white list(s) 220 for other communication devices 310, etc.). Characteristics of femto coverage allowance can be set or pre-set through the access management component 225.

Subsequent to allowance and examination of information related to relevant white list(s) 220, access management component 235 can update white list(s) 220, which can be stored in data storage 245, to reflect the approved request for femto coverage by the femto AP 130. It is to be noted that access and update of collected subscriber identifier numbers (e.g., MSISDN), codes or token, can also be effected through network-based white list database(s). The white list(s) 220 can be updated to include desired information regarding the communication device(s) 310, where the information can include, for example, identifier numbers, codes, or token of the communication device(s) 310, type of communication device(s) 310, services that can be utilized by the communication device(s) 310, type of access granted and/or the subset services associated with the femto AP 130 for which access is granted, type of technologies (e.g., communication technologies) supported by the communication device(s), bandwidth requirements of the communication device(s) 310, bandwidth allocated to the communication device(s) 310, QoS policy associated with the communication device(s) 310, time the communication device(s) 310 is entered on the white list(s) 220, and/or historical data (e.g., usage data related to use of the femto AP 130 by the communication device(s) 310), etc.

In an aspect, when a communication device 310 is placed (e.g., stored) in the white list(s) 220 on a temporary basis, information related to the communication device 310 can remain on the white list(s) 220 until a specified condition(s) is met. The specified condition can comprise, for example, the communication device 310 temporarily remains on the white list(s) 220 for a predetermined amount of time (or a specified extended amount of time when the communication device 310 requests and is granted an extended amount of time), the communication device 310 temporarily remains on the white list(s) 220 until the communication device 310 leaves the coverage area of the femto AP 130, and/or the communication device 310 temporarily remains on the white list(s) 222 until the communication device 310 is powered down (e.g., turned off, battery discharged, . . . ) or re-booted, as desired. Once a specified condition is met, the access management component 235 can facilitate updating the white list(s) 220 to delete information related to the communication device 310 from the white list(s) 220, and the updated white list(s) 220 can be stored in data storage 245.

In another aspect, the access management component 235 can grant access to a subset of services associated with the femto AP 130 to the communication device 310 that is granted access to the femto AP 130. The services contained in the subset of services can be determined based at least in part on the predefined access criteria. The services can include, for example, voice services (e.g., wireless mobile phone services), data services (e.g., messaging, Internet access, etc.), accessing applications, electronic gaming, and/or accessing or downloading content (e.g., video content, audio content, images, multimedia content, . . . ). In an aspect, the predefined access criteria can relate to, for example, information stored in a white list(s) associated with the femto AP 130, the services available from the femto AP 130, type of communication device 310, bandwidth available to be allocated to the communication device 310, services that can be utilized by the communication device 310, historical data associated with the communication device(s) 310 in relation to the femto AP 130, QoS, type of technologies (e.g., communication technologies) supported by the communication device(s), type(s) of service(s) requested by the communication device (s), etc.

In an aspect, the services that can be associated with and/or provided via the femto AP 130 can be as desired, and can include, for example, voice services (e.g., wireless mobile phone calls), data services (e.g., messaging, Internet access, . . . ), applications, electronic gaming, and/or access to content (e.g., audio content, video content, multimedia content, . . . ). The femto AP 130 also can be connected (e.g., wired wirelessly) to electronic devices in addition to communication devices, where the electronic devices can comprise, for example, digital video recorders/players, digital music recorders/players, analog video recorders/players (with digital conversion), analog music recorders/players (with analog conversion), electronic games, televisions, set-top boxes, cameras (e.g., digital cameras), and/or a navigation system or device (e.g., global position satellite (GPS) system.

An illustrative, non-limiting advantage of example system 300 is that it can provide an enhanced end user experience with a direct, clear mechanism and thus can encourage use of the femto AP 130, and can avoid time spent on edition of white list(s) through a networked interface (e.g., interface component 210) like an online interface which can take time for the end user to have access to the Internet, and to log on in a secured interface.

In another aspect, if the request for access by the communication device(s) 310 is rejected by the access management component 235 or the communication device 310 indicates that the communication device 310 desires to opt out of accessing the femto AP 130, or if the access management component 235 determines that there is no available slot in the femto AP 130 (and associated white list(s) 220), the access management component 235 can deny access of the femto AP 130 to the communication device 310. In still another aspect, when access is denied, the communication device 310 can be placed on a black list(s) 222 associated with the femto AP 130, on a permanent (or semi-permanent) or temporary basis, for example, by the access management component 235, where the black list(s) 222 can be stored in data storage 245. For instance, if the access management component 235 receives a message from the communication device 310 that indicates the communication device 310 desires to permanently (or semi-permanently) opt out of coverage by the femto AP 130 and/or if the access management component 235 determines that the communication device 310 is not to be granted access to coverage by the femto AP 130 on a permanent basis based at least in part on predefined access criteria, the access management component 235 can facilitate updating the black list(s) 222, and storing the black list(s) 222 in data storage 245, to include information related to the communication device 310, where the communication device 310 can be listed in the black list(s) 222 on a permanent (or semi-permanent) basis.

In yet another aspect, if the communication device 310 communicates a message to the femto AP 130 that indicates that the communication device 310 is opting out of coverage by the femto AP 130 at this time, but not on a permanent basis, or if access to the femto AP 130 is denied by the access management component 235 (e.g., due to no available slot on the white list(s)), the black list(s) 222 can be updated to include information related to the communication device 310 on the black list(s) 222 on a temporary basis, for example, by the access management component 235, where the black list(s) 222 can be stored in data storage 245. In an aspect, a communication device 310 on the black list(s) 222 on a temporary basis can remain on the black list(s) 222 until a predefined black-list condition(s) is met. The predefined black-list conditions can comprise, for example, the communication device 310 temporarily remains on the black list(s) 222 for a predetermined amount of time, the communication device 310 temporarily remains on the black list(s) 222 until the communication device 310 leaves the coverage area of the femto AP 130, and/or the communication device 310 temporarily remains on the black list(s) 222 until the communication device 310 is powered down (e.g., turned off, battery discharged, . . . ) or re-booted, as desired. Once a black-list condition is met, the access management component 235 can facilitate updating the black list(s) 222 to delete information related to the communication device 310 from the black list(s) 222, and the updated black list(s) 222 can be stored in data storage 245.

While on the black list(s) 222 (temporarily or permanently (or semi-permanently)), the communication device 310 is not eligible for access to or to attempt access to the femto AP 130. Employing black list(s) 222 can facilitate reducing signaling (e.g., unnecessary signaling) between communication devices and the femto AP 130, as it will be unnecessary for signaling by the femto AP 130 to a black-listed communication device with regard to the black-listed communication device accessing the femto AP 130; can facilitate reduced power consumption by the femto AP 130 and/or the black-listed communication device due in part to the reduced signaling; and can facilitate more efficient communication between the femto AP 130 and communication devices 310 in the coverage area of the femto AP 130, since unnecessary signaling can be reduced.

It is to be appreciated that a request for access can be effected by the femto AP 130 automatically, through an access management component (e.g., access management component 225), for example. Also, substantially any wireless communication device 310 within coverage area of femto AP 130 (e.g., area 125) can request access without intervention by a subscriber that operates femto AP 130, and who has previously entered a set of subscriber station numbers (e.g., MSISDNs), codes or tokens, via a networked interface (e.g., interface component 210). Alternatively, or in addition, a request for access can be prompted by a device utilized by a subscriber that operates the femto AP. Once a request is granted, a secure tunnel can be established from the device/client through the femtocell's IP connection or the default of the Radio Access Network if the IP connection is not available. Secure layers including utilizing the femtocell's VPN and/or USSD would ensure that the transaction is in fact secure.

As a non-limiting example, a temporary visitor or employee (e.g., a babysitter) who is coming over to a location served by a femto access point (e.g., femto AP 130) for a limited period of time, can be provided with coverage via the femto AP by a subscriber that operates the femtocell so the employee can perform, at least in part, his/her work activities (e.g., provide updates on behavior of children) through utilization of the femto access point. In case the subscriber fails to know identifier numbers, codes or tokens for devices the employee can utilize, and the subscriber is not interested in going through the process of requesting and entering the numbers, codes or tokens via a networked interface to allow coverage for the limited period of time that the employee performs work, the employee (e.g., babysitter) can convey a request (e.g., query 815) to the femto AP to facilitate allowing the employee to request femto access directly from the employee's communication device when in range of the femto AP.

Figure 4:
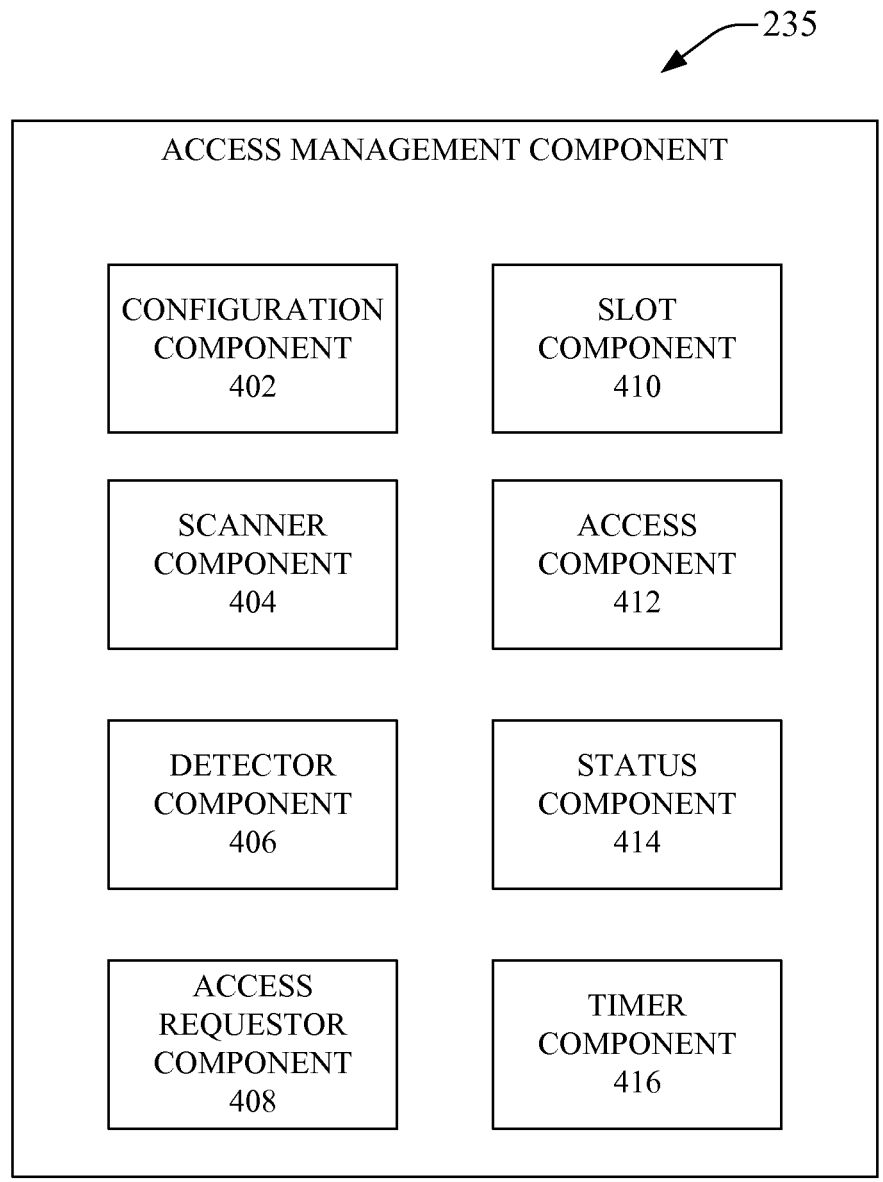
FIG. 4 is a block diagram an example access management component that can facilitate management of an access control list(s) and access of subscribers and subscriber stations to a femtocell in accordance with an aspect of the disclosed subject matter.

FIG. 4 depicts a block diagram of an example access management component 235 that can facilitate management of an access control list(s) and access of subscribers and subscriber stations to a femtocell in accordance with an aspect of the disclosed subject matter. In an aspect, the access management component 235 can comprise a configuration component 402 that can facilitate generating, configuring, and/or updating a white list(s) 220 (e.g., an access control list(s)) and/or a black list(s) 222 associated with femto AP 130. The configuration component 402 can receive information associated with a communication device(s) (e.g., 310) that is or has been within the coverage area of the femto AP 130. The configuration component 402 can receive the information associated with the communication device(s) from the communication device or via an interface component (e.g., 210) and/or other networked interfaces (e.g., voice or sound commanded interface(s), touch commanded interface(s), biometric commanded interfaces(s), etc.). The received information can be utilized to generate, configure, and/or update a white list(s) 220 and/or black list(s) 222 based at least in part on the information related to the communication device(s), information already contained in a white list(s) and/or black list(s), predefined access criteria, and/or other information.

In another aspect, the access management component 235 can include a scanner component 404 that can scan a frequency spectrum in which communication devices can occupy and communicate to facilitate detecting communication devices 310 that enter the cell coverage area (e.g., area 125) of the femto AP 130. The access management component 235 also can include a detector component 406 that can detect communication devices 310 that enter the cell coverage area of the femto AP 130. The detector component 406 can facilitate identifying a particular communication device 310 based at least in part on detected or received information from the particular communication device 310.

In another aspect, the access management component 235 can contain an access requestor component 408 that can facilitate automatically generating requests or prompts for access to the femto AP 130 that can be transmitted to communication devices 310 detected in the femto coverage area, and/or can receive requests to access the femto AP 130 and associated services from communication devices 310 in the femto coverage area. In still another aspect, the access management component 235 can include a slot component 410 that can facilitate managing slots associated with the femto AP 130 (e.g., slot(s) in the white list(s) 220 and/or correspondingly in the femto AP 130) and determining availability of a slot associated with a femto AP 130 when a communication device desires to access the femto AP 130 and services associated therewith.

In yet another aspect, the access management component 235 can comprise an access component 412 that can facilitate controlling granting access of the femto AP 130 to a communication device and granting access to a subset of services associated with the femto AP 130 to the communication device. The granting of access can be based at least in part on predefined access criteria associated with the femto AP 130.

In an aspect, the access management component 235 can include a status component 414 that can facilitate determining whether a communication device 310 is to be stored in a white list(s) 220 or black list(s) 222 on a temporary basis or a permanent basis. The status component 414 also can facilitate monitoring or tracking the status of a communication device 310 that is accessing the femto AP 130 and/or associated services, and/or can monitor other components associated with the access management component 235 or femto AP 130. For example, the status component 414 can monitor whether a communication device 310, which is temporarily on the white list(s) 220, is still active in the cell coverage area of the femto AP 130. If the communication device 310 is no longer active in the cell coverage area (e.g., communication device 310 has left the cell coverage area, communication device 310 is turned off, . . . ), the status component 414 can determine that the communication device 310 is to be removed from the white list(s) 220, and the configuration component 402 can update the white list(s) 220 to delete information related to the communication device 310 from the white list(s) 220.

In yet another aspect, the access management component 235 can contain a timer component 416 that can be utilized to facilitate tracking the time that a particular communication device 310 has been on a white list(s) 220 or a black list(s) 222 associated with the femto AP 130. The timer component 416 can comprise a desired number of timers that can be employed with regard to respective communication devices 310 in the cell coverage area and temporarily on a white list(s) 220 or black list(s) 222 to facilitate tracking the respective amounts of time that each of those communication devices 310 have been listed in the respective white list(s) 220 or black list(s) 222, and/or have been accessing the femto AP 130 and/or an associated subset of services (e.g., for communication device(s) 310 temporarily on the white list(s) 220).

In view of the example systems described herein, example methodologies that can be implemented in accordance with the disclosed subject matter can be better appreciated with reference to flowcharts in FIGS. 5-9. For purposes of simplicity of explanation, example methodologies disclosed herein are presented and described as a series of acts; however, it is to be understood and appreciated that the claimed subject matter is not limited by the order of acts, as some acts may occur in different orders and/or concurrently with other acts from that shown and described herein. For example, a methodology disclosed herein could alternatively be represented as a series of interrelated states or events, such as in a state diagram. Moreover, interaction diagram(s) may represent methodologies in accordance with the disclosed subject matter when disparate entities enact disparate portions of the methodologies. Furthermore, not all illustrated acts may be required to implement a methodology in accordance with the subject specification. It should be further appreciated that the methodologies disclosed throughout the subject specification are capable of being stored on an article of manufacture to facilitate transporting and transferring such methodologies to computers for execution by a processor or for storage in a memory.

Figure 5:
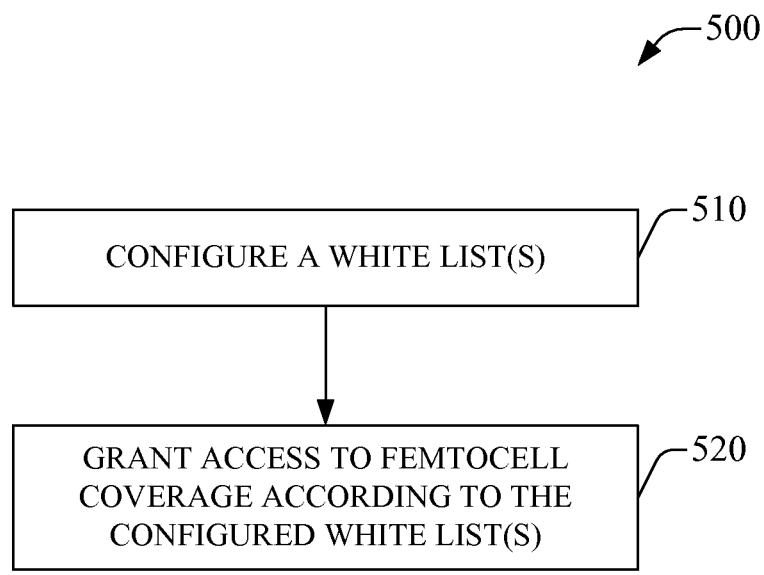
FIG. 5 illustrates a flowchart of an example methodology for managing access of subscribers and subscriber stations to cell coverage in accordance with an aspect of the disclosed subject matter.

FIG. 5 presents a flowchart of an example methodology 500 for managing access of subscribers and subscriber stations to cell (e.g., femtocell) coverage in accordance with an aspect of the disclosed subject matter. At 510, a white list(s) (e.g., access control list(s)) associated with a femtocell can be configured. In an aspect, configuration of the white list(s) (e.g., 220) can be performed via a networked interface, interactively or automatically based at least in part on operation conditions of the femtocell. The configuration of the white list(s) can relate to, for example, initial provisioning of the femtocell, capturing of wireless communication devices (e.g., 310), responding to request for access by a communication device, updating extant access control lists, and so forth. At 520, access to cell (e.g., femtocell) coverage can be granted at least in part according to the configured white list(s). In another aspect, the configured white list(s) can possess an associated profile that can facilitate controlling logic for utilization of the white list(s), via a set of parameters that can determine conditions of access to the femto AP 130 and associated subset of services, type of access to the femto AP 130 and associated subset of services, subset of services available to a particular communication device or associated user of communication device, etc.

Figure 6:
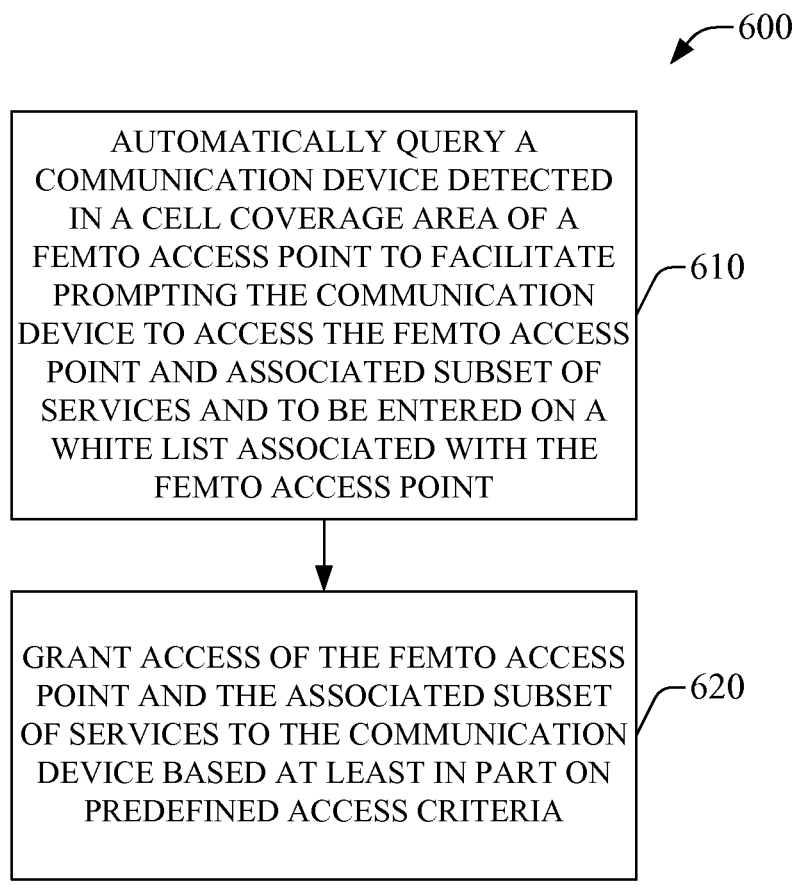
FIG. 6 illustrates a flowchart of an example methodology for managing access of subscribers and subscriber stations to cell coverage in accordance with an aspect of the disclosed subject matter.

FIG. 6 illustrates a flowchart of an example methodology 600 that can employ interactive white list (e.g., access control list) prompting of an access point (e.g., femto AP) to facilitate managing access of subscribers and subscriber stations (e.g., communication devices) to femtocell coverage and associated services in accordance with an aspect of the disclosed subject matter. At 610, a query can be automatically generated and transmitted to a communication device detected in a cell coverage area of a femto AP 130, where the query can prompt the communication device to access the femto AP 130 and associated subset of services provided via the femto AP 130 and to be entered on a white list associated with the femto AP 130. In an aspect, the access management component 235 can facilitate automatically generating and transmitting the query to a detected communication device 310 to facilitate automatically populating the white list 220.

In an aspect, the communication device 310 can enter a cell coverage area of a femto AP 130. The femto AP 130 can scan for communication devices in the cell coverage area and can detect the communication device. The femto AP 130 can query the communication device to inquire whether the communication device desires to connect to the femto AP 130 and be entered in a white list(s) associated with the femto AP 130. A user of the communication device can desire to opt in (or opt out) to connecting with the femto AP 130 and inclusion on the associated white list(s) to enable the communication device to access certain services and/or content associated with a femto AP 130.

At 620, access to a subset of services associated with the femto AP 130 can be granted to the communication device in the cell coverage area associated with the femto AP 130 based at least in part on predefined access criteria. In an aspect, the predefined access criteria can relate to information stored in a white list(s) associated with the femto AP 130, whether the communication device (e.g., user of the communication device) desires to opt in to access the femto AP 130 and associated subset of services, availability of a slot(s) of the femto AP 130 (and associated white list(s)) to which the communication device can be connected, the services available from the femto AP 130, type of communication device, bandwidth available to be allocated to the communication device, etc.

In another aspect, if and when the communication device 310 desires to access the femto AP 130 and is approved for access by the access management component 235, information related to the communication device 310 can be stored in the white list(s) 220 (e.g., access control list(s)) associated with the femto AP 130, where the information can be stored temporarily or permanently in the white list(s) (e.g., 220), as desired.

Figure 7:
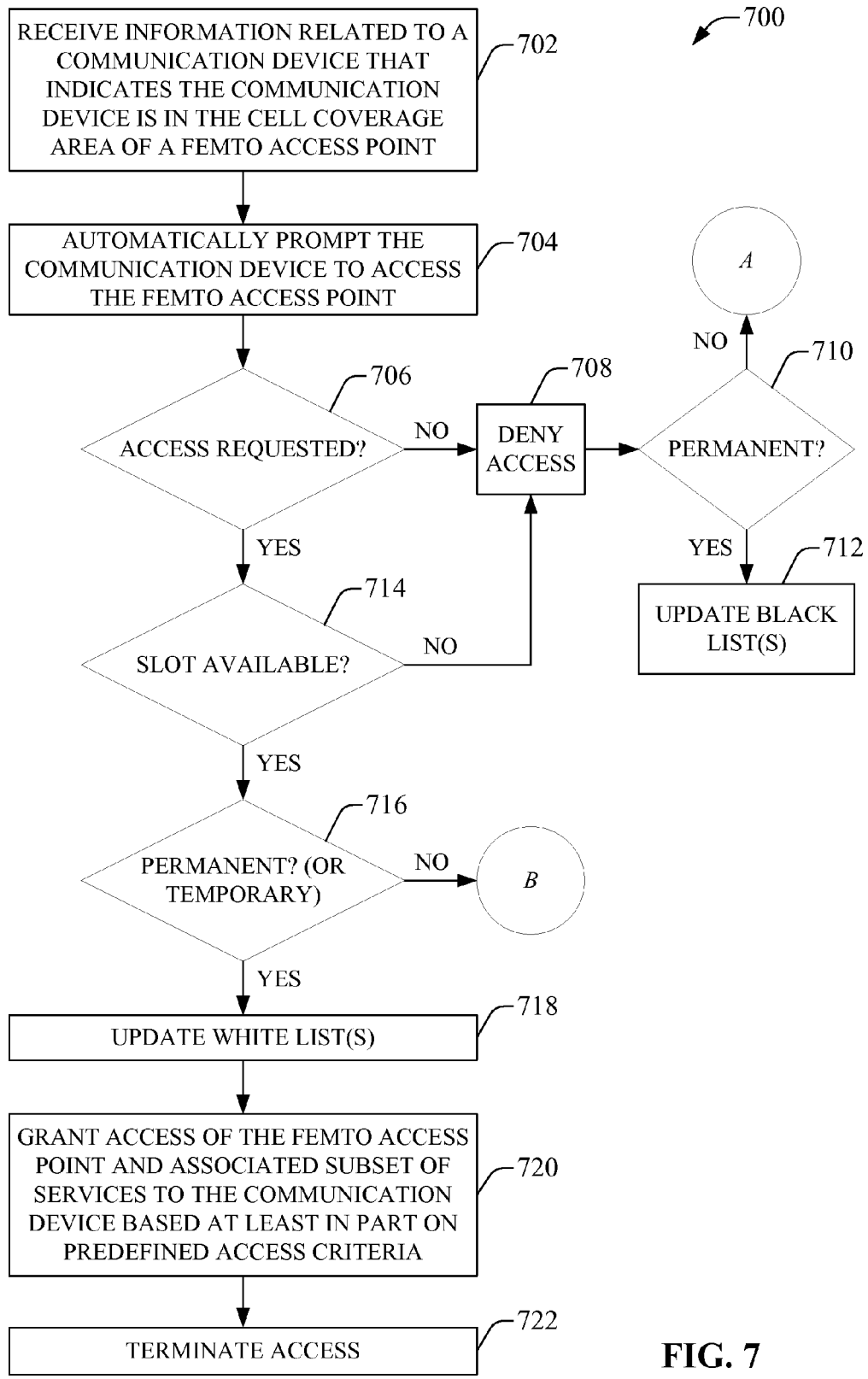
FIG. 7 illustrates a flowchart of an example methodology that can employ interactive white list prompting by an access point to facilitate automatically populating a white list(s) associated with a femtocell and managing access of subscribers and subscriber stations to femtocell coverage and associated services in accordance with an aspect of the disclosed subject matter.

FIG. 7 illustrates a flowchart of an example methodology 700 that can employ interactive white list prompting by an access point (e.g., femto AP 130) to facilitate automatically populating a white list(s) associated with a femtocell and managing access of subscribers and subscriber stations (e.g., communication devices 310) to femtocell coverage in accordance with an aspect of the disclosed subject matter. At 702, information related to a communication device (e.g., 310) can be received, where the received information can indicate that the communication device is in the cell (e.g., femtocell) coverage area of a femto AP 130, for example. For instance, a femto AP 130 can scan a frequency spectrum to facilitate detecting wireless communication devices (e.g., cellular phone, computer, . . . ) that are in the cell coverage area of the femto AP 130. A wireless communication device can enter the cell coverage area when a user carries the communication device into the cell coverage area, and the femto AP 130 can detect and/or identify the communication device based at least in part on identification information (e.g., device number, code, or token such as MSISDN) associated with the communication device. The femto AP 130 also can identify (e.g., automatically, via query) other information associated with the communication device, such as type of communication device, compatible communication technologies of the communication device, types of services that the communication device can utilize, etc.

At 704, the communication device can be automatically prompted to access (or to request access of) the femto AP 130. In an aspect, in response to detecting the communication device 310, the access management component 235 of the femto AP 130 can automatically generate and transmit a query, via the communication platform 255, to the detected communication device 310 to prompt the communication device 310 to access, or at least request access of, the femto AP 130 and associated services. In one aspect, the femto AP 130 can be configured to automatically query detected communication devices 310 to facilitate populating the white list(s) associated with the femto AP 130. In another aspect, the femto AP 130 can automatically query a communication device 310 detected in the cell coverage area to inquire whether the communication device desires to access the femto AP 130, be entered on a white list(s) associated with the femto AP 130, and access services associated with (e.g., available via) the femto AP 130. It is to be appreciated and understood that, in accordance with various other aspects, the communication device 310 can transmit a request to access the femto AP 130, or a subscriber of the femto AP 130 can utilize the femto AP 130 or another device associated therewith to query the communication device 310 to inquire whether the communication device 310 desires access to the femto AP 130.

At 706, a determination can be made regarding whether the communication device requests access to the femto AP 130 (e.g., based in part on an automatic prompt to access the femto AP 130). If, at 706, it is determined that the communication device does not desire access to the femto AP 130, at 708, access to the femto AP 130 by the communication device can be denied. In an aspect, the femto AP 130 can transmit a message indicating that access is not granted to the communication device 310. Access to the femto AP 130 can be denied due to the user of the communication device 310 denying the invitation to connect to the femto AP 130 or due to predefined access criteria associated with the femto AP 130. For example, the access management component 235 can identify the communication device 310 using the device identifier information and can determine this communication device 310 is not to be granted access (e.g., prior abuses when accessing the femto AP 130).

At 710, a determination can be made regarding whether the communication device is denied access to the femto AP 130 on a permanent (or semi-permanent) basis or a temporary basis. In an aspect, the femto AP 130 can transmit a request as to whether the user of the communication device 310 desires to opt out of accessing the femto AP 130 on a permanent or semi-permanent (e.g., where the opting out of access to the femtocell can be reversed) basis, or desires to opt out of accessing the femto AP 130 on a temporary basis. In another aspect, the femto AP 130 can determine whether the communication device 310 is to be denied access to the femto AP 130 on a permanent (or semi-permanent) basis based at least in part on the communication device 310, the user of the device 310, or other desired access criteria. For example, the owner of the femto AP 130 can desire to deny access to a particular user of a communication device 310, and, if the particular user and associated communication device 310 enter the cell coverage area, the identification information of the communication device 310 can be recognized by the femto AP 130 and the femto AP 130 can facilitate denying access to the communication device 310 on a permanent basis.

If, at 710, it is determined that the communication device is to be denied access to the femto AP 130 on a permanent (or semi-permanent) basis, at 712, a black list(s) can be updated to facilitate indicating that the communication device is denied access to the femto AP 130 permanently (or semi-permanently). If, at 710, it is determined that the communication device is not to be denied access to the femto AP 130 on a permanent (or semi-permanent) basis (e.g., user of communication device desires to temporarily refuse access to the femto AP 130 at this time), methodology 700 can proceed to reference point A, where a black list(s) can be updated to temporarily block access of the femto AP 130 to the communication device, as disclosed more fully herein with regard to methodology 800.

Referring again to reference numeral 706, if, at 706, it is determined that the communication device requests access to the femto AP 130, at 714, a determination can be made regarding whether any slot(s) is available. In an aspect, the access management component 235 can facilitate determining whether the white list(s) 220 has a slot available in which the communication device 310 can be listed (and femto AP 130 has any slot available to which the communication device 310 can be connected). If, at 714, it is determined that no slot is available, methodology 700 can proceed to reference numeral 708, where access of the femto AP 130 and associated subset of services by the communication device can be denied. In an aspect, the femto AP 130 can transmit a message, which can indicate that access is not granted, to the communication device 310.

If, at 714, it is determined that there is a slot(s) available, at 716, a determination can be made regarding whether the communication device is be placed on the white list(s) permanently or temporarily. If it is determined that the communication device is to be placed on the white list(s) temporarily, methodology 700 can proceed to reference point B, where the white list(s) can be updated to include the communication device on a temporary basis, as disclosed more fully herein with regard to methodology 900. For example, the user of the communication device 310 can desire to be on the white list(s) 220 temporarily because the user intends to utilize the femto AP 130 on a limited basis (e.g., only one time).

If, at 716, it is determined that the communication device is to be placed on the white list(s) permanently, at 718, the white list(s) can be updated to include information related to the communication device and/or associated user. In an aspect, the access management component 235 can facilitate updating the white list(s) to store desired information (e.g., identification information, account information, communication device information, services that can be exploited by the communication device 310, services for which the communication device 310 is granted access, user information, QoS, and/or bandwidth allocation, etc.) related to the communication device 310 and/or associated user in the white list(s), where the white list(s) can be stored in data storage 245.

At 720, the communication device can be granted access to the femto AP 130 and a subset of services associated with the femto AP 130 based at least in part on the predefined access criteria. In an aspect, the access management component 235 can facilitate granting access to a subset of services (e.g., voice services, data services, access of applications, electronic gaming, access or downloading/sharing of content, etc.) associated with the femto AP 130 to the communication device 310 based at least in part on the white list(s), the user of the communication device 310, the type of communication device 310, available bandwidth of the femto AP 130, and/or other desired access criteria. For example, an owner or operator of the femto AP 130 can desire to limit access of a communication device 310 of the owner/operator's child to a specified subset of services that is suitable for children. As another example, the owner/operator of the femto AP 130 can desire to limit access to certain services, and not allow access to other services, by a communication device 310 due to current bandwidth availability. In still another example, the owner/operator of the femto AP 130 can desire to allow access to a first subset of services to the owner/operator and other trusted or desired entities (e.g., spouse, friends, . . . ) using respective communication devices and allow access to a disparate subset of services to other entities (e.g., visitors using respective communication devices) to which access is granted, where the first subset of services can contain more services than the disparate subset of services. The user of the communication device 310 can utilize the subset of services associated with the femto AP 130 to which access is granted.

At 722, access to the femto AP 130 can be terminated. In an aspect, access of the communication device 310 to the femto AP 130 (and the subset of services) can be terminated due in part to the communication device 310 leaving the cell coverage area, the femto AP 130 receiving a request to terminate access from the communication device 310, the communication device 310 entering an off state (e.g., turned off, battery discharged, etc.) or is re-booted, etc. At this point, the communication device 310 can no longer access the femto AP 130 and associated subset of services unless the femto AP 130 again grants the communication device 310 access. The information related to the communication device 310 and associated user can be maintained (e.g., stored) in the white list(s) 220.

Figure 8:
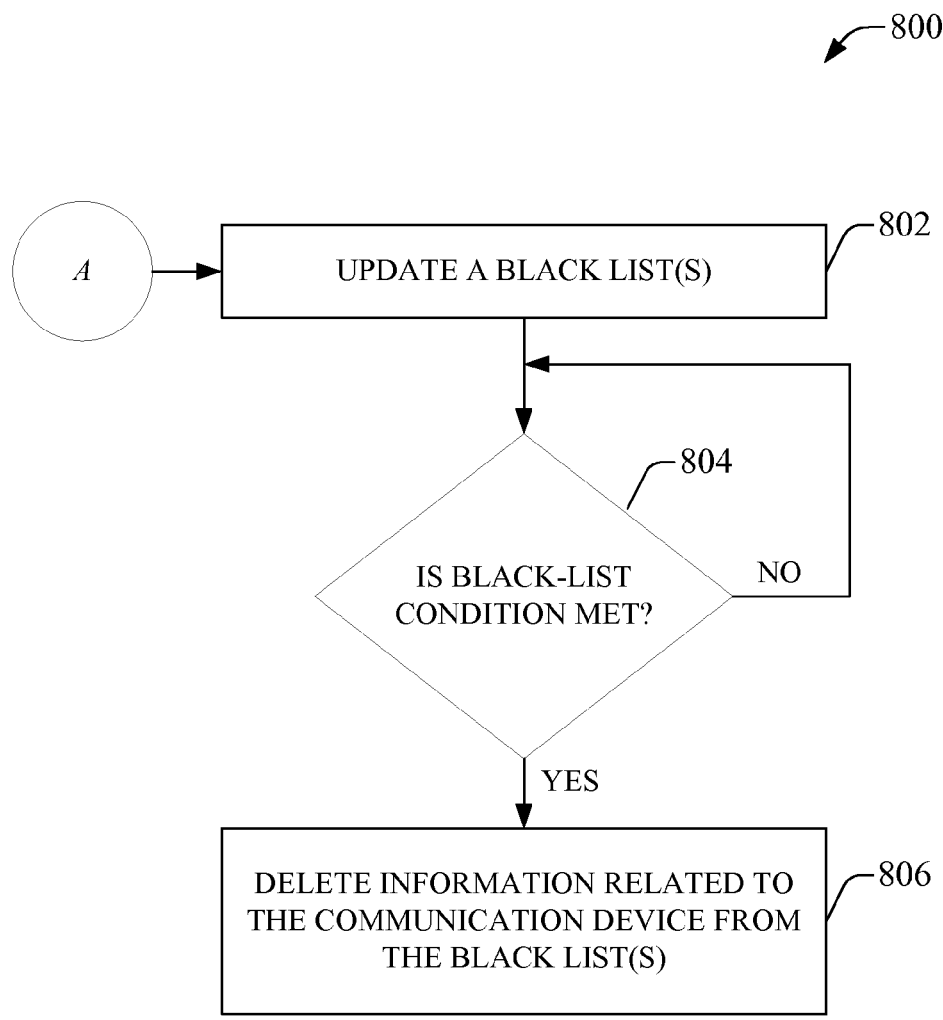
FIG. 8 depicts a flowchart of an example methodology that can manage a black list(s) to facilitate managing access of subscribers and subscriber stations to femtocell coverage in accordance with an aspect of the disclosed subject matter.

FIG. 8 depicts a flowchart of an example methodology 800 that can manage a black list(s) to facilitate managing access of subscribers and subscriber stations to femtocell coverage in accordance with an aspect of the disclosed subject matter.

Methodology 800 can proceed from reference point A, where at reference point A in methodology 700, it was determined that a communication device is to be placed on a black list(s) associated with a femto AP 130 on a temporary basis. Proceeding from reference point A, at 802, a black list(s) can be updated. In an aspect, an access management component 235 can update a black list(s) associated with the femto AP 130 to store (e.g., temporarily store) information (e.g., identification information, account information, communication device information, user information, etc.) related to the communication device and/or associated user. For instance, the user of the communication device can desire to refuse access to the femto AP 130 at a particular time, but does not want to permanently be denied access to the femto AP 130, so the user can transmit information indicating that the user does not desire access to the femto AP 130 at this time. As a result, the access management component 235 can determine that the communication device is to be temporarily placed on the black list(s) associated with femto AP 130 to facilitate reducing signaling or other transmissions between the femto AP 130 and communication device while the communication device is in the cell coverage area, which can facilitate reducing power consumption by the femto AP 130 and communication device, and can facilitate more efficient communication between the femto AP 130 and other communication devices in the cell coverage area.

At 804, a determination can be made regarding whether a black-list(s) condition is met. In an aspect, the access management component 235 can determine whether a black-list(s) condition has been met to facilitate determining whether the communication device is to be removed from the black list(s). For instance, a black-list(s) condition can be that the communication device remains on the black list(s) 222 for a predefined period of time, the communication device remains on the black list(s) 222 until the communication device leaves the cell coverage area, the communication device is re-booted or powered down (e.g., turned off, battery discharged), and/or other access criteria, as desired. For example, a timer can be employed to facilitate determining the amount of time the communication device is on the black list(s) 222. The access management component 235 can receive information from the timer and can monitor the amount of time the communication device has been on the black list(s) 222. If, at 804, it is determined that a black-list(s) condition is not met, methodology 800 can proceed to reference numeral 804, where methodology 800 the communication device and/or the timer can be monitored to facilitate determining whether a black-list(s) condition is met.

If, at 804, it is determined that a black-list(s) condition is met, at 806, the communication device can be deleted from the black list(s). For instance, if the communication device meets one or more applicable black-list(s) conditions, such as, for example, the communication device is on the black list(s) 222 for a predefined period of time, the communication device leaves the cell coverage area, the communication device is re-booted or powered down, and/or other desired access criteria, the communication device can be eligible to be removed from the black list(s) 222, and the access management component 235 can facilitate deleting information related to the communication device and associated user from the black list(s) 222. The updated black list(s) 222 can be stored in the data storage 245.

Figure 9:
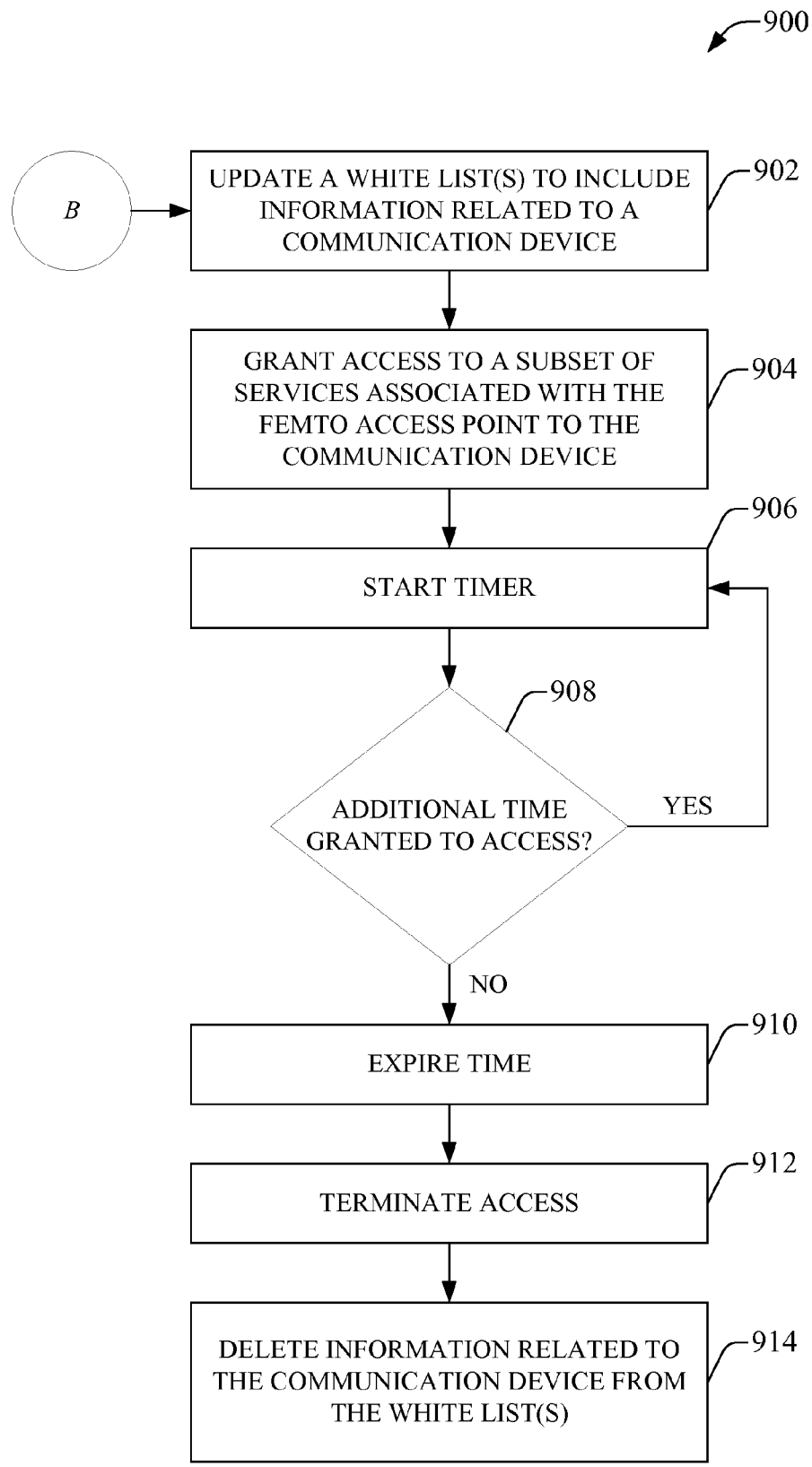
FIG. 9 depicts a flowchart of an example methodology that can temporarily store information related to a subscriber station and associated subscriber in a white list(s) to facilitate managing access of subscribers and subscriber stations to femtocell coverage in accordance with an aspect of the disclosed subject matter.

FIG. 9 depicts a flowchart of an example methodology 900 that can temporarily store information related to a subscriber station and associated subscriber in a white list(s) (e.g., access control list(s)) to facilitate managing access of subscribers and subscriber stations (e.g., communication devices 310) to femtocell coverage in accordance with an aspect of the disclosed subject matter. Methodology 900 can proceed from reference point B, where at reference point B in methodology 700, it was determined that a communication device is to be placed on a white list(s) associated with a femto AP 130 on a temporary basis. Proceeding from reference point B, at 902, the white list(s) can be updated to include information related to the communication device and/or associated user. In an aspect, the access management component 235 can facilitate updating the white list(s) 220 to store information (e.g., identification information, account information, communication device information, user information, etc.) related to the communication device and/or associated user in the white list(s) 222, which can be stored in data storage 245.

At 904, the communication device can be granted access to a subset of services associated with the femto AP 130. In an aspect, the access management component 235 can facilitate granting access to a subset of services associated with the femto AP 130 to the communication device based at least in part on the white list(s) 220, the user of the communication device, the type of communication device, available bandwidth of the femto AP 130, and/or other desired access criteria. For example, an owner or operator of the femto AP 130 can desire to limit access of a communication device of the owner/operator's child to a specified subset of services that is suitable for children. The user of the communication device can utilize the subset of services associated with the femto AP 130 to which access has been granted.

At 906, a timer can be started. In an aspect, the access management component 235 can employ a timer component 412 that can employ a timer(s) that can be utilized to facilitate tracking the amount of time that the communication device has been stored in the white list(s) 220 and/or accessing the subset of services. At 908, a determination can be made regarding whether additional time is to be granted to the communication device to access the subset of services and to remain on the white list(s). In an aspect, the access management component 235 can facilitate communicating a message to the communication device to inquire whether the user of the communication device desires additional time for the communication device to access the subset of services (and remain on the white list(s) 220). The access management component 235 can determine whether to grant the communication device additional time to access the subset of services (and remain on the white list(s) 220) based at least in part on the response to the inquiry received from the communication device and/or other desired access criteria.

If, at 908, it is determined that additional time is granted to enable access the subset of services by the communication device (and for the communication device to remain on the white list(s) 220), methodology 900 can return to reference numeral 906, where the timer (e.g., of timer component 412) can be started (e.g., re-started), and methodology 900 can proceed from that point. In an aspect, the amount of additional time granted to the communication device can be the same or different as the initial amount of time granted to the communication device, as desired.

If, at 908, it is determined that additional time is not granted to the communication device with regard to accessing the subset of services (and remaining on the white list(s) 220), at 910, time related to granting of access to the communication device (and storing information related to the communication device and associated user on the white list(s) 220) can expire. In an aspect, the access management component 235 can receive an indication from the timer component 412 that the amount of time granted to the communication device to access the subset of services associated with the femto AP 130 and to be stored on the white list(s) 220 associated with the femto AP 130 has expired.

At 912, access to the subset of services by the communication device can be terminated. In an aspect, the access management component 235 can facilitate terminating access to the subset of services associated with the femto AP 130 by the communication device. At this point, the communication device will no longer be able to utilize the subset of services. At 914, information related to the communication device and associated user can be deleted from the white list(s). In an aspect, the access management component 235 can facilitate deleting information related to the communication device and its user from the white list(s) 220. In another aspect, when information related to the communication device 310 is stored in a white list(s) 220 on a temporary basis, the access management component 235 can facilitate deleting information related to the communication device 310 from the white list(s) 220 when another specified condition is met, where the specified condition can comprise, for example, the communication device 310 leaves the cell coverage area of the femto AP 130, the communication device is powered down or rebooted, and/or the communication device 310 is otherwise not detected to be in the cell coverage area of the femto AP 130. Maintenance of the white list(s) 220 to remove information related to communication devices that are temporarily stored on the white list(s) 220 can facilitate efficient communication between the femto AP 130 and communication devices in the cell coverage area.

Figure 10:
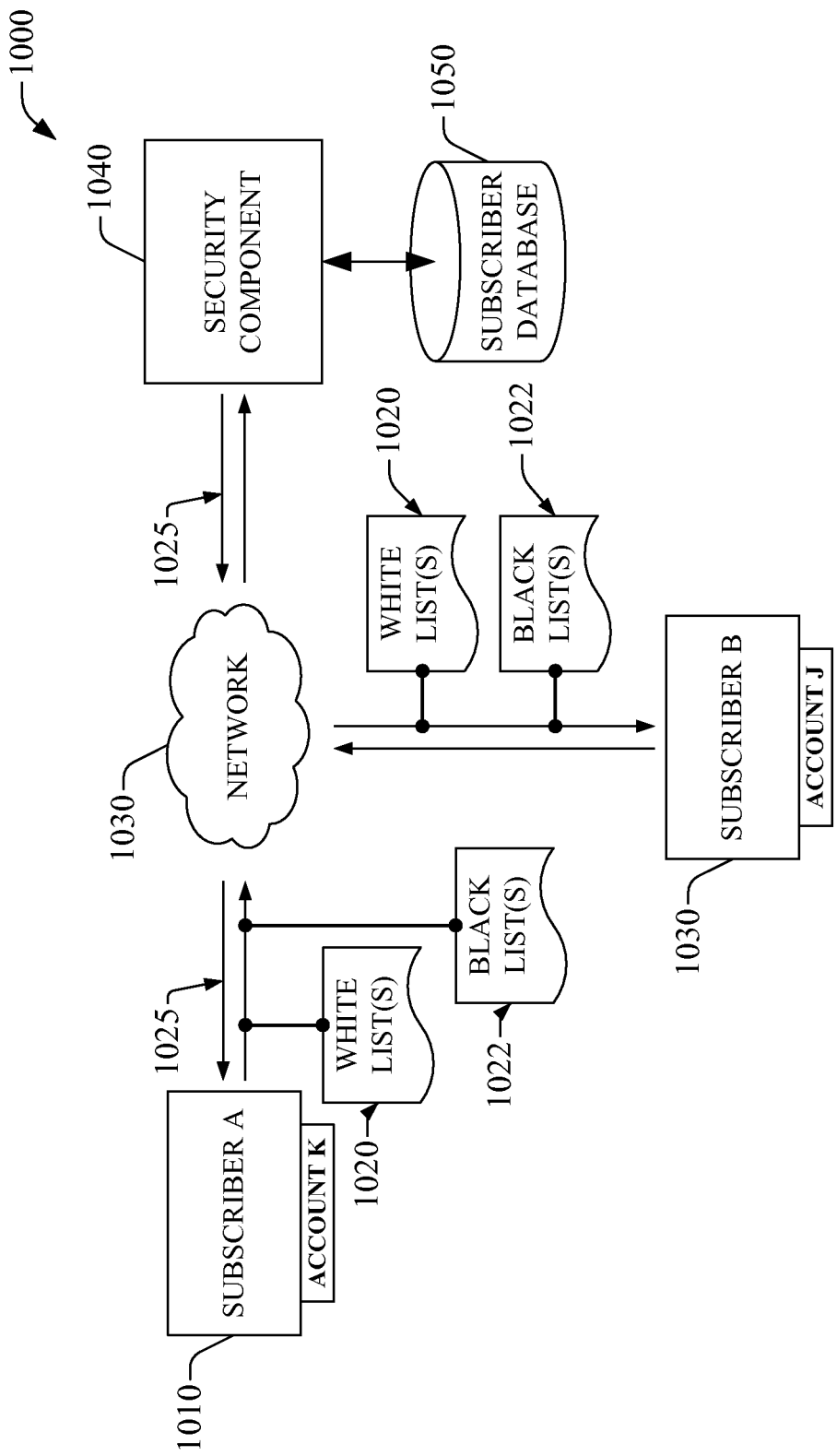
FIG. 10 is a block diagram of an example system that can facilitate sharing white list(s) and/or black list(s) among subscribers of a wireless network service in order to provide straightforward access configuration to, and activation of, a femtocell among femtocell subscribers.

FIG. 10 is a block diagram of an example system 1000 that can facilitate sharing white list(s) (e.g., access control list(s)) and/or black list(s) among subscribers of a wireless network service in order to provide straightforward access configuration to, and activation of, a femtocell (e.g., femto AP 130) among femtocell subscribers. Subscribers can belong to disparate or same service accounts with either a macro service provider or femto provider, or both. For example, subscribers that share white list(s) 1020 and/or black list(s) 1022 can pertain to a group or family associated with a single service account. In example system 1000, subscriber A 1010 who belongs to account K can convey white list(s) 1020 and/or black list(s) 1022 over network 1030, via a wired or wireless link 1025, to subscriber B 1030 who belongs to account J. Subscriber A 1010 can hide or eliminate specific subscriber station numbers from white list(s) 1020 and/or black list(s) 1022 he/she/it grants to other subscribers. It should be appreciated that the granting of subscriber station numbers, codes or tokens can substantially reduce the amount of time to configure, or set up a white list(s) 1020 and/or black list(s) 1022, as opposed to manually re-entering multiple numbers, codes, or tokens (e.g., up to 50 numbers, codes or tokens) across multiple femtocells.

A security component 1040, or authorization layer, can facilitate ensuring that unauthorized mobile subscriber numbers, codes or tokens, respectively associated with communication devices (e.g., 310) are not provided when not approved by end users. Such approval can be determined via a specified privacy policy associated with the end user, or subscriber, which can be stored in a subscriber database 1050; the specified privacy policy can be configured/updated through various means, such as, for example, web-based interfaces, call center, text-message center, etc. Security component 1040 can ensure privacy integrity when white list(s) 1020 and/or black list(s) 1022 are shared among subscribers of different accounts (e.g., J≠K). In an illustrative aspect, security component 1040 can solicit subscribers outside a "white-list share" (or "black-list share") originating account to grant the authority for their subscriber station identifier number, code or token to be shared through white list(s) 1020 (or black list(s) 1022). To the latter end, security component 1040 can resort to various mechanisms that can include, but are not limited to including, a short message service (SMS) communication, a multimedia message service (MMS) communication, email, voice mail, web pop up, etc. Alternatively, or in addition, security component 1040 can mitigate security mechanism(s) complexity through validation via subscriber account information (e.g., stored in subscriber database 1050) in order to grant automatic access to a white list(s) 1020 and/or black list(s) 1022 within groups or families underneath a single service account, without additional security verification.

Figure 11:
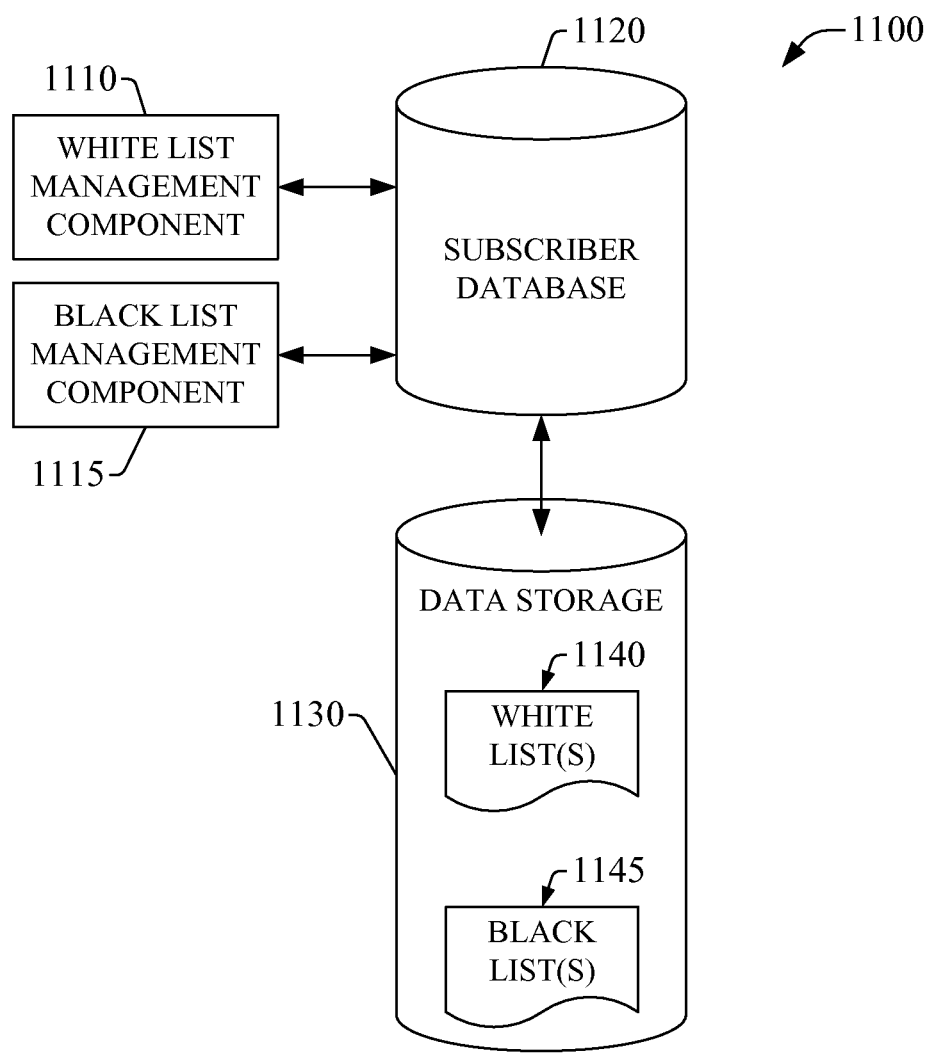
FIG. 11 is a block diagram of an example system that can facilitate management of a white list(s) and a black list(s) associated with a femtocell in accordance with an aspect of the disclosed subject matter.

FIG. 11 is a block diagram of an example system 1100 that can facilitate management of a white list(s) (e.g., an access control list(s)) and a black list(s) associated with a femtocell (e.g., femto AP 130) in accordance with an aspect of the disclosed subject matter. System 1100 can comprise a white list management component 1110 that can access a subscriber database 1120 which can be maintained by a service operator for femto and macro cells, and a data storage 1130 that retains a set of white lists 1140 associated with serviced subscribers, to associate white-listed subscribers across disparate white lists. Such association can lead to genesis of white-lists trees. In an aspect, the white list management component 1110 can implement mechanisms to facilitate mitigating exponential data growth and efficient storage of white-list trees like data-compression (e.g., wavelet, efficient tree representation, and so on), distributed data warehouses, and so forth.

In another aspect, system 1100 can comprise a black list management component 1115 can access a subscriber database 1120 which can be maintained by a service operator for femto and macro cells, and a data storage 1130 that can retain a set of black lists 1145 associated with serviced subscribers, to associate black-listed subscribers across disparate black lists. Such association can lead to genesis of black-lists trees. In an aspect, the black list management component 1115 can implement mechanisms to facilitate mitigating exponential data growth and efficient storage of black-list trees like data-compression (e.g., wavelet, efficient tree representation, and so on), distributed data warehouses, etc.

In still another aspect, the white list management component 1110 can deploy a white-list tree in accordance to the following illustrative, non-limiting scenario. (i) User 1 adds User 2 to his/her white list (e.g., 1140). (ii) User 2 adds User 3 to his/her white list (e.g., 1140). (iii) User 1 and User 3 can be associated through the respective white lists. (iv) User 1 and User 3 can match User 4 extant on each other's white lists. (v) User 1 and User 3 can associate User 5 that is on User 4's white list. White list management component 1110 can effect associations and manage generated white-list tree(s). It should be appreciated that substantially any association, hierarchical or non-hierarchical, or deployment of white lists 1140 can be implemented by the white list management component 1110 through information stored in subscriber database 1120 and data storage 1030. It is to be appreciated and understood that the black list management component 1115 similarly can deploy a black-list tree in accordance with the above illustrative, non-limiting scenario.

An illustrative, non-limiting advantage of structured, hierarchical generation of white lists to subscribers (e.g., subscriber A 1010) is that more subscribers can have access to femtocells (e.g., femto APs 130) to gain coverage enhancement, or have access to added value through unlimited usage on any femtocell or unique services available via a set of femtocells.

In addition, example system 1100 can track subscriber station identifier numbers (e.g., MSISDNs), codes or tokens, associated with white list(s) on record with a femto service provider. White list management component 1110 can validate white list(s) 1140, stored in data storage 1130, against current accounts and associated subscriber station identifier numbers (e.g., MSISDNs), codes, or tokens, for a service provider. In particular, when a subscriber, or end user, cancels an account with a service provider, white list(s) 1140 can be updated according to information retrieved from subscriber database 1120, or substantially any other database available to a service provider that contains information on service subscribers. In addition, when an end user changes their mobile or subscriber station number, code or token, (e.g., after relocation to a new area code, or the like) substantially all white list(s) 1140 that the mobile or subscriber station number, code or token is associated with can automatically be updated by the white list management component 1110.

An illustrative advantage of such automatic update of white list(s) 1140 is ease of use for end users to maintain current white list(s) 1140 without a need to keep track of each subscriber station number, code or token associated with the white list(s) 1140. In addition, updated white list(s) 1140 can maintain the value proposition of the femtocells for end users and service operator by a seamless move of traffic off of the macro network (e.g., a WAN) to femto network(s).

In accordance with an embodiment, the white list management component 1110 can facilitate distinguishing between communication devices (and associated users) that are temporarily on a white list 1140 of a subscriber as compared to communication devices (and associated users) that are permanently on the white list 1140 of the subscriber when a white list 1140, or subset thereof, of one subscriber is added to a white list 1140 of another subscriber. For instance, the white list management component 1110 can facilitate selecting or associating subscribers that are permanently on a white list 1140 of one subscriber, but not selecting or associating subscribers that are temporarily on the white list 1140 of the one subscriber, and adding a subset of the white list of the one subscriber (e.g., the selected or associated subscribers that are permanently on the white list) to the white list 1140 of the other subscriber. It is to be appreciated and understood that the black list management component 1115 similarly can select a desired subset of subscribers on one black list 1145 of one subscriber (e.g., selecting subscribers that are permanently on a black list of the one subscriber, but not subscribers that are temporarily on the black list of the one subscriber) and adding the subset of subscribers to the black list 1145 of another subscriber when in accordance with the embodiment.

Figure 12:
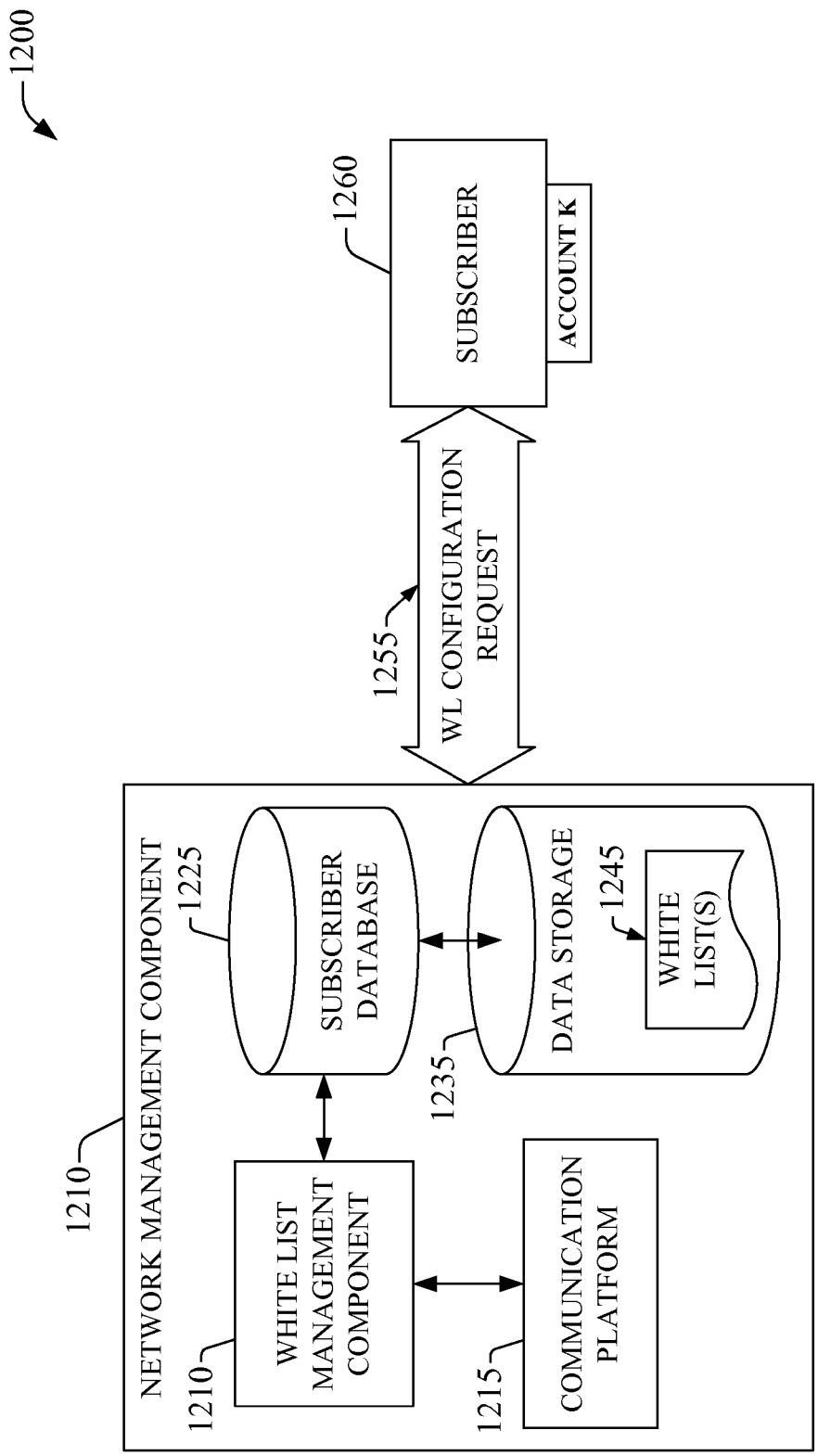
FIG. 12 illustrates a block diagram of an example system that can facilitate addition of subscriber(s)/subscriber station (s) to one or more white lists associated with a femtocell in accordance with an aspect of the disclosed subject matter.

FIG. 12 is a block diagram of an example system 1200 that can facilitate addition of subscriber(s)/subscriber station(s) to one or more white lists associated with a femtocell (e.g., femto AP 130) in accordance with an aspect of the disclosed subject matter. In example system 1200, a network management component 1210 can include a white list management component 1210 which can be coupled to a subscriber database 1225, a data storage 1235, and a communication platform 1215. The white list management component 1210 can data-mine subscriber database 1225 and white list(s) 1245, which can reside in data storage 1235, to drive addition of new subscribers to a white list to request reciprocal adding. In an aspect, once a subscriber 1260 in account K is identified for reciprocal addition at a time the subscriber 1260 configures his/her femto AP (e.g., 130), a white list (WL) configuration request 1255 can be conveyed (e.g., via a wired or wireless link through communication platform 1215) to the subscriber. Such configuration request can indicate that a disparate subscriber has subscriber 1260 white-listed and can prompt subscriber 1260 to include in his/her white list the disparate subscriber.

An illustrative scenario is the following: User 1 adds User 2 to his/her white list. Once User 2 configures/activates his/her femtocell, a setup process (e.g., implemented through a web-based online GUI) can prompt User 2 to add User 1. It is to be noted that the white list management component 1210 can exploit information in subscriber database 1225 and data storage 1235 to inform User 2 of substantially all subscriber station numbers, codes or tokens that he/she can automatically add to his/her white list on a reciprocity basis; namely, User 2 can be prompted to add in the white list(s) of User 2 those subscribers that have previously added him/her to their white list(s). In an aspect, the white list configuration request 1255 can be effected through one or more of various interfaces, such as an online GUI; a real time prompt/alert delivered via SMS, MMS, email, instant message; etc.

Figure 13:
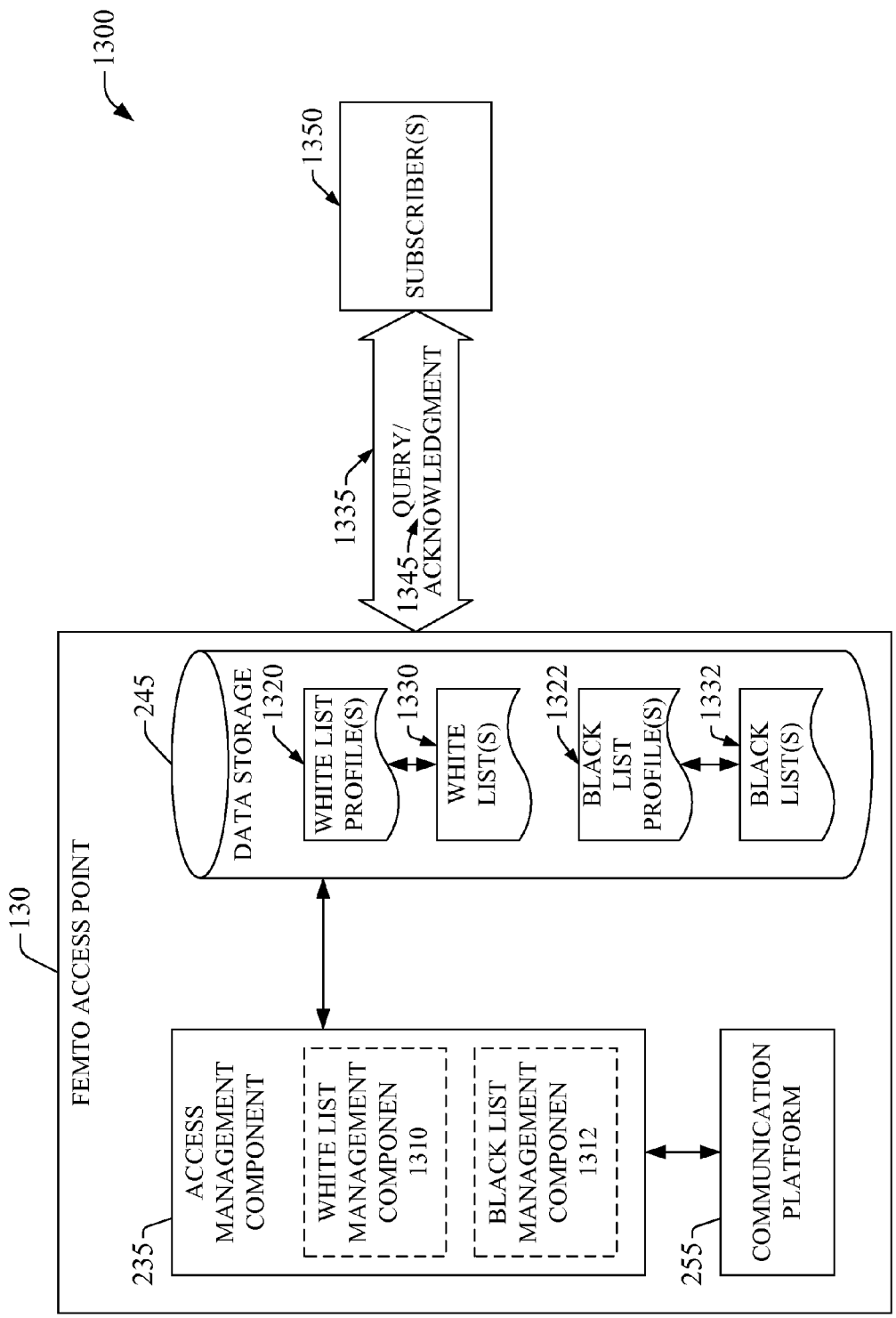
FIG. 13 depicts a block diagram of an example system that can manage a defined logic relating to maintaining content(s) in a white list(s) on a white list database and a black list(s) in a black list database in accordance with an aspect of the disclosed subject matter.

FIG. 13 is a block diagram of an example system 1300 that can manage a defined logic relating to maintaining content(s) (e.g., MSISDNs) in a white list(s) (e.g., access control list(s)) on a white list database and a black list(s) in a black list database in accordance with an aspect of the disclosed subject matter. In an aspect, the access management component 235, which can comprise a white list management component 1310, can develop a white list profile(s) 1320 that can apply logic and parameters that can facilitate controlling, or managing, content, such as subscriber station numbers (e.g., MSISDNs), codes or tokens, in a white list(s) 1330. White list profile(s) 1320 and white list(s) 1330 can be stored in data storage 245; it should be appreciated that while data storage 245 is illustrated to reside within femto AP 130, such storage can reside in a network management component (e.g., component 1210).

In another aspect, white list profile parameters that can facilitate controlling utilization logic of white list(s) content can include, without being limited to including: (i) temporary access, e.g., full access for a specific time interval, such as a specified number of days, hours, or minutes; (ii) access only within a window of time in a day (e.g., voice and data allowed from 9:00 a.m.-6:00 p.m., or voice allowed after 9:00 p.m.) which can facilitate billing schemes already established by an operator/service provider); and/or (iii) access to specific applications, such as scheduler, calendar(s), news streaming, authoring tools, gaming, video and music, etc.

In still another aspect, logic within white list profile(s) can implement parameters to determine how long access to femto coverage is granted. For instance, when a timer associated with temporary access of a subscriber station (e.g., communication device) expires, a query 1345 can be conveyed (e.g., through a wired or wireless link 1335) to either a subscriber that operates a device associated with the managed MSISDN in order to request renewed access, or to a subscriber that operates femto AP 130. The message request, e.g., query 1345, can ask the owner if an extension of time is to be granted or not. When a request is not granted by a subscriber that operates femto AP 130 or there is no reply, e.g., acknowledgement 1345, from the subscriber, access to femto coverage can expire and information, such as the MSISDN (or substantially any identifier code or token), associated with the subscriber station can be deleted from a corresponding white list(s) within data storage 245. Conversely, a positive response, e.g., acknowledgement 1345, can allow access to continue for the subscriber station based at least in part on parameters extant in white list profile(s) or newly defined parameters. It is to be noted that query 1345 can be conveyed via an online GUI, an email message, a SMS message, MMS message, a voice mail, a web prompt, and the like.

In yet another aspect, the access management component 235 can comprise a black list management component 1312 and can develop a black list profile(s) 1322 that can apply logic and parameters that can facilitate controlling, or managing, content, such as subscriber station numbers (e.g., MSISDNs), codes or tokens, in a black list(s) 1332. The black list profile(s) 1322 and black list(s) 1332 can be stored in data storage 245.

In an aspect, black list profile parameters that can facilitate controlling utilization logic of block list(s) content can include, without being limited to including: temporary denial of access of the femto AP by the subscriber station until a black-list condition(s) is met, where the black-list condition(s) can comprise information related to the subscriber station (e.g., 310) temporarily remains on the black list(s) 1332 for a predetermined amount of time, information related to the subscriber station temporarily remains on the black list(s) 1332 until the subscriber station 310 leaves the coverage area of the femto AP, and/or information related to the subscriber station temporarily remains on the black list(s) 1332 until the subscriber station is powered down (e.g., turned off, battery discharged, . . . ) or re-booted; and/or permanent (or semi-permanent) denial of access of the femto AP by the subscriber station. When a black-list condition(s) is met, denial of access to femto coverage can expire and information, such as the MSISDN (or substantially any identifier code or token), associated with the subscriber station can be deleted from a corresponding black list(s) within data storage 245.

Figure 14:
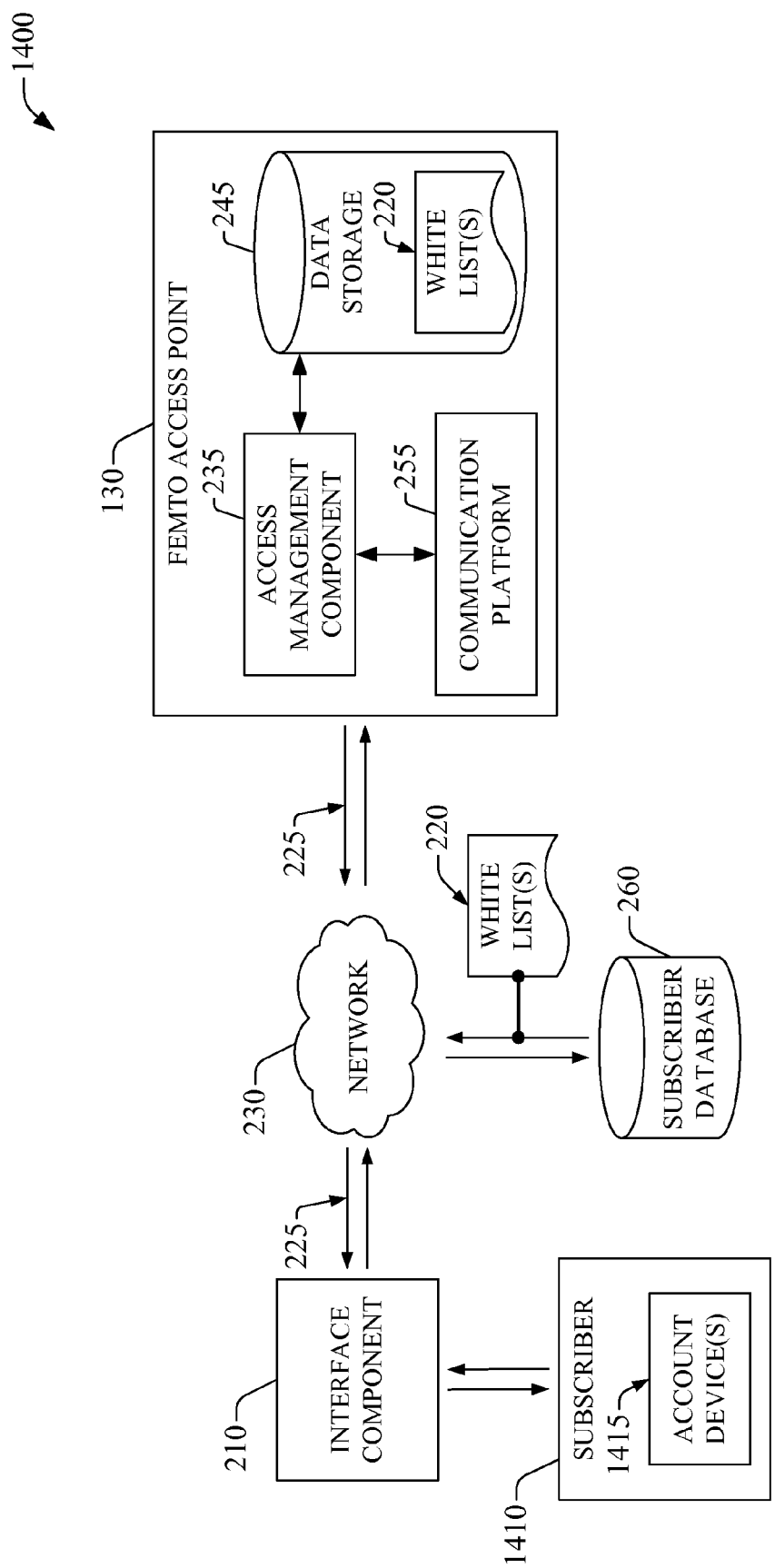
FIG. 14 illustrates a block diagram of an example system that can initialize a white list(s) to femto coverage for a subscriber station with available subscriber station identifier numbers, codes or tokens available on a service account in accordance with an aspect of the disclosed subject matter.

FIG. 14 is a block diagram of an example system 1400 that can initialize a white list(s) (e.g., access control list(s)) to femto coverage for a subscriber station with available subscriber station identifier numbers, codes or tokens available on a service account in accordance with an aspect of the disclosed subject matter. In example system 1400, a subscriber 1410 who can utilize account device(s) 1415, can provision femto AP 130 and associate the account device(s) 1415 with a service account via a networked interface component 210 (e.g., an online account management system) which can look up into substantially all subscriber station(s) identifier numbers (e.g., MSISDNs), codes or tokens associated with the service account, and can automatically populate white list(s) 220 with the extracted subscriber station(s) numbers, codes or tokens. Subscriber 1410, via interface component 210, can remove or add subscriber station(s) numbers (e.g., MSISDNs), codes or tokens extant in a pre-populated white list(s) 220; additional edits can be performed as well, based at least in part on the complexity of white list(s) 220. In an aspect, to pre-set white list(s) 220, the networked interface component 210 can access information stored in subscriber database 260 through network 230, which can include information technology systems of a service provider. White list(s) 220 can be conveyed through network 230 to femto AP 130; a communication platform 255 can receive white list(s) 220 and access management component 235 can store the white list(s) 220 in data storage 245.

Illustrative advantages provided by example system 1400 can include (a) reduced femtocell provisioning lead time, and (b) immediate utilization of a femtocell with mobile numbers that belong to a same service account, whether subscribers of such numbers subscribe to the femtocell or a feature application, or code, that delivers a femtocell service.

Figure 15:
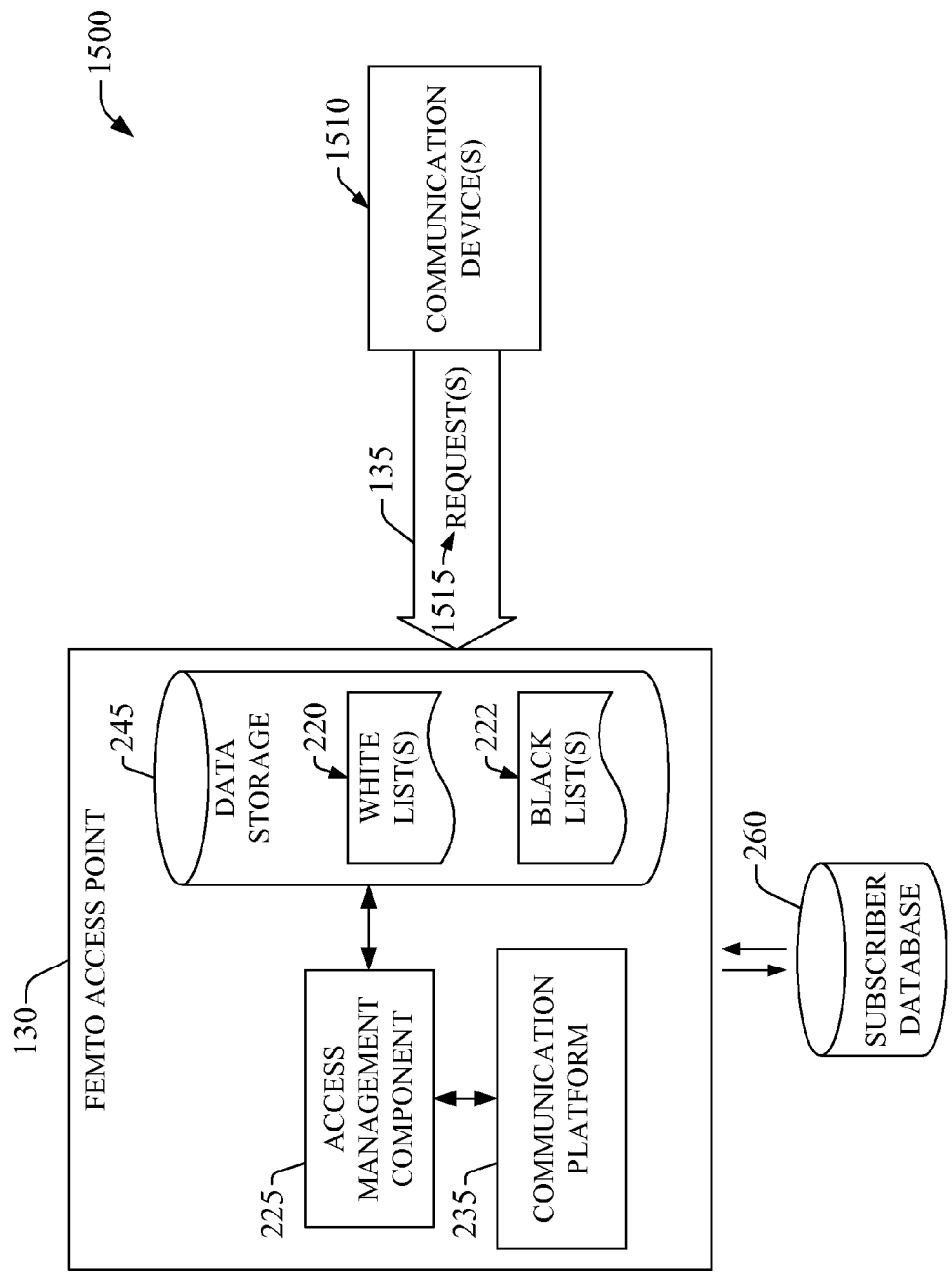
FIG. 15 depicts a block diagram of an example system that can facilitate management of access of a femto access point by a communication device on a request from the communication device in accordance with an aspect of the disclosed subject matter.

FIG. 15 is a block diagram of an example system 1500 that can facilitate management of access of a femto AP by a communication device on a request from the communication device in accordance with an aspect of the disclosed subject matter. In example system 1500, communication device(s) 1510 (e.g., such as a mobile phone subscriber station(s), such as a mobile phone (e.g., UE 120$_A$), computer that can communicate in a wireless environment (e.g., subscriber station 120$_B$), or other wireless mobile communication device) can convey a request or query 1515 to facilitate accessing coverage of femto AP 130. The query 1515 can be conveyed via an online GUI, an email message, a SMS message, MMS message, a voice mail, a web prompt, USSD (or * and # codes), and the like. Such request 1515 can be received by communication platform 255, and access management component 235 can be configured to allow or reject the request; allowance or rejection of a request can be based at least in part on various metrics, such as security, type of communication device, profile of subscriber that operates/operated the communication device 1510 that requests access, etc. Upon allowance of a request, the access management component 235 can query for available slots to be filled in white list(s) 220 associated with accounts served by femto AP 130, and when space is available for a subscriber station identifier number (e.g., MSISDN), code or token, the query can further probe whether access is allowed on a permanent or temporary basis (e.g., to reduce risk exposure to security problems, maintain available space on white list(s) 220 for other communication devices 1510, etc.). Characteristics of femto coverage allowance can be set or pre-set through the access management component 225. Subsequent to allowance and examination of information related to relevant white list(s) 220, access management component 235 can update white list(s) 220, stored in data storage 245, to reflect the approved request for femto coverage by the femto AP 130. It is to be noted that access and update of collected subscriber identifier numbers (e.g., MSISDN), codes or token, can also be effected through network-based white list database(s). Information (e.g., wireless device numbers, codes or tokens (e.g., MSISDNs); subscriber's active numbers, codes or tokens; and numbers, codes or tokens on service accounts in good standing, . . . ) related to communication devices 310 can be provided through networked access to a subscriber database 260.

An illustrative, non-limiting advantage of example system 1500 is that it can provide an enhanced end user experience with a direct, clear mechanism and thus can encourage use of the femto AP 130, and can avoid time spent on edition of white list(s) through a networked interface (e.g., interface component 210) like an online interface which can take time for the end user to have access to the Internet, and to log on in a secured interface.

In another aspect, if the request 1515 is rejected by the access management component 235, or if there is no available slot in the white list(s) 220 and associated femto AP 130, the access management component 235 can deny access of the femto AP 130 to the communication device 1510. The communication device 1510 also can be placed on a black list(s) 222 associated with the femto AP 130, and stored in data storage 245, on a permanent (or semi-permanent) or temporary basis, for example, by the access management component 235. For instance, if the access management component 235 determines that the communication device 1510 is not to be granted access to coverage by the femto AP 130 on a permanent basis based at least in part on predefined access criteria, the access management component 235 can facilitate updating the black list(s) 222, and storing the black list(s) 222 in data storage 245, to include information related to the communication device 1510, where the communication device 1510 can be listed in the black list(s) 222 on a permanent (or semi-permanent) basis.

In yet another aspect, if access to the femto AP 130 is denied by the access management component 235 at this time (e.g., due to no available slot on the white list(s)), the black list(s) 222 can be updated to include information related to the communication device 1510 on the black list(s) 222 on a temporary basis, for example, by the access management component 235, where the black list(s) 222 can be stored in data storage 245. The communication device 1510 can remain on the black list(s) 222 until a predefined black-list condition(s) is met. The predefined black-list conditions can comprise, for example, the communication device 1510 temporarily remains on the black list(s) 222 for a predetermined amount of time, the communication device 1510 temporarily remains on the black list(s) 222 until the communication device 1510 leaves the coverage area of the femto AP 130, and/or the communication device 1510 temporarily remains on the black list(s) 222 until the communication device 1510 is powered down (e.g., turned off, battery discharged, . . . ) or re-booted, as desired. Once a black-list condition is met, the access management component 235 can facilitate updating the black list(s) 222 to delete information related to the communication device 1510 from the black list(s) 222, and the updated black list(s) 222 can be stored in data storage 245.

While on the black list(s) 222 (temporarily or permanently (or semi-permanently)), the communication device 1510 is not eligible for access to or to attempt access to the femto AP 130. Employing black list(s) 222 can facilitate reducing signaling (e.g., unnecessary signaling) between communication devices and the femto AP 130, as it will be unnecessary for signaling by the femto AP 130 to a black-listed communication device with regard to the black-listed communication device accessing the femto AP 130; can facilitate reduced power consumption by the femto AP 130 and/or the black-listed communication device due in part to the reduced signaling; and can facilitate more efficient communication between the femto AP 130 and communication devices 310 in the coverage area of the femto AP 130, since unnecessary signaling can be reduced.

It is to be appreciated that substantially any wireless communication device 1510 within coverage area of femto AP 130 (e.g., area 125) can request access without intervention by a subscriber that operates femto AP 130, and who has previously entered a set of subscriber station numbers (e.g., MSISDNs), codes or tokens, via a networked interface (e.g., interface component 210). Once a request is granted, a secure tunnel can be established from the device/client through the femtocell's IP connection or the default of the Radio Access Network if the IP connection is not available. Secure layers including utilizing the femtocell's VPN and/or USSD would ensure that the transaction is in fact secure.

Figure 16:
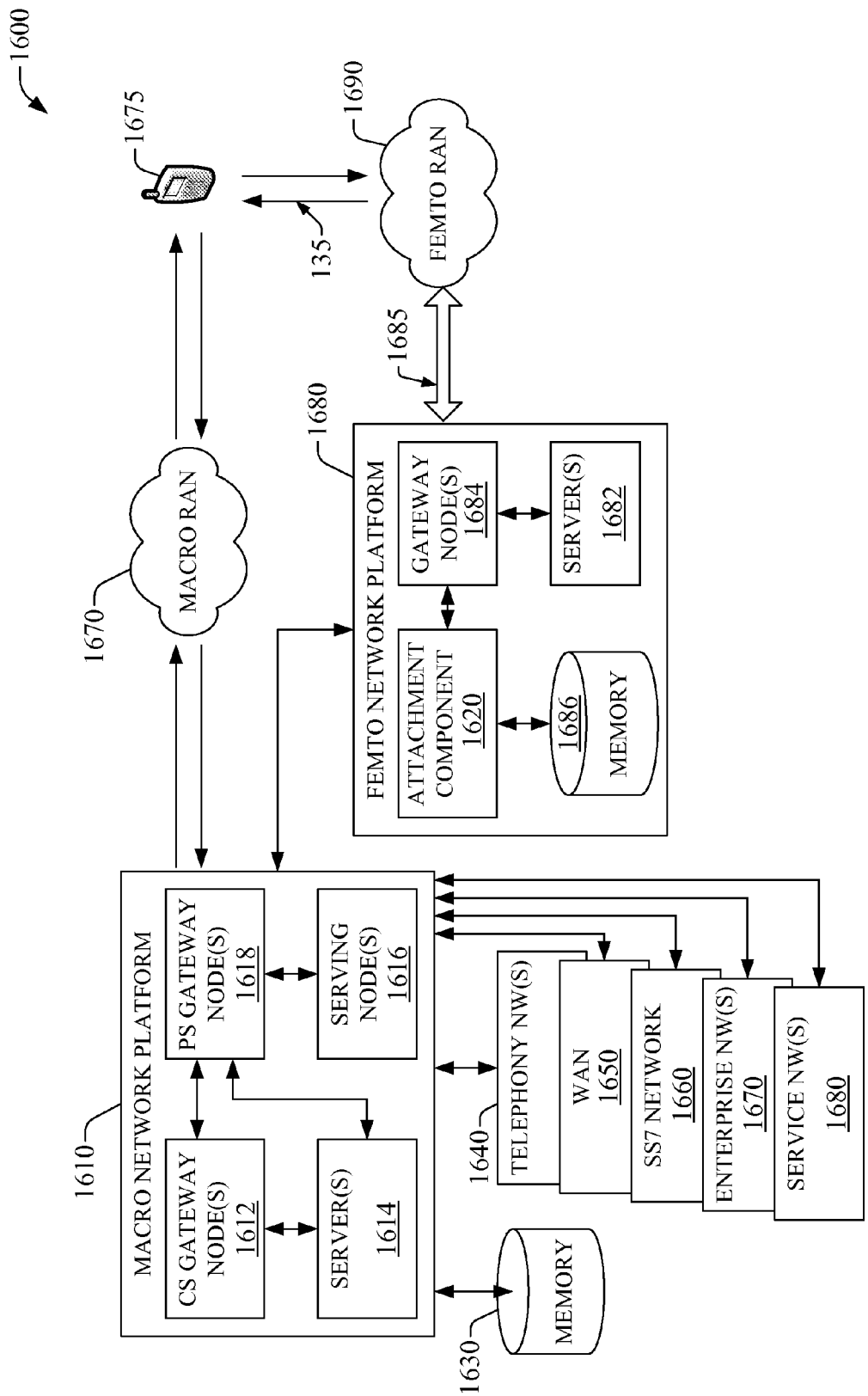
FIG. 16 depicts a block diagram of example macro and femto wireless network environments that can exploit femto APs in accordance with various aspects of the disclosed subject matter.
Figure 17:
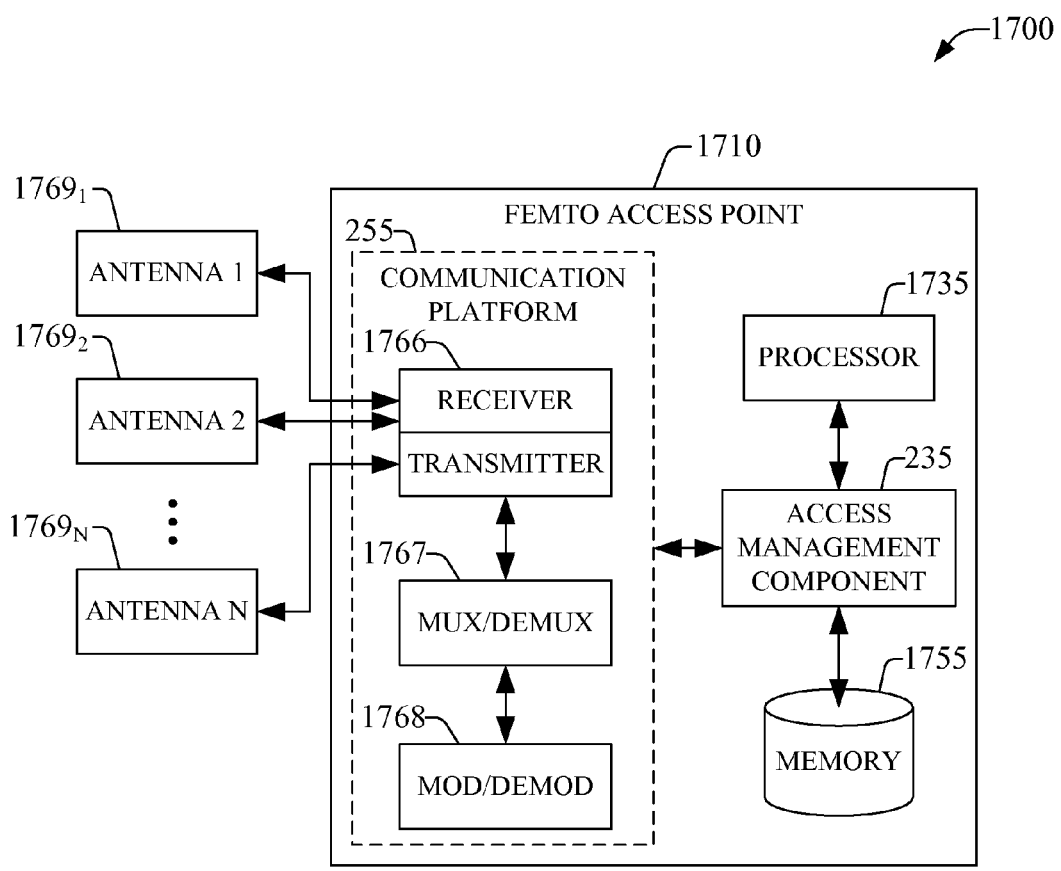
FIG. 17 is a block diagram of an example femto access point that operates in accordance with aspects disclosed in the subject specification.

To provide further context for various aspects of the subject specification, FIG. 16 and FIG. 17 illustrate, respectively, example macro and femto wireless network environments that can exploit femto APs and a block diagram of an example embodiment of a femtocell access point that can enable and exploit features or aspects of the subject innovation and that utilize aspects of the subject innovation in accordance with various aspects of the subject specification.

With respect to FIG. 16, wireless communication environment 1600 includes two wireless network platforms: (i) A macro network platform 1610 which serves, or facilitates communication with user equipment 1675 (e.g., mobile 120$_A$) via a macro radio access network (RAN) 1670. It should be appreciated that in cellular wireless technologies (e.g., 3GPP UMTS, HSPA, 3GPP LTE, 3GPP2 UMB), macro network platform 1610 is embodied in a Core Network. (ii) A femto network platform 1680, which can provide communication with UE 1675 through a femto RAN 1690, which is linked to the femto network platform 1680 via backhaul pipe(s) 1685 (e.g., backhaul link(s) 153). It should be appreciated that macro network platform 1610 typically hands off UE 1675 to femto network platform 1610 once UE 1675 attaches (e.g., through macro-to-femto handover) to femto RAN 1690, which includes a set of deployed femto APs (e.g., femto AP 130) that can operate in accordance with aspects described herein.

It is noted that RAN includes base station(s), or access point(s), and its associated electronic circuitry and deployment site(s), in addition to a wireless radio link operated in accordance with the base station(s). Accordingly, macro RAN 1670 can comprise various coverage cells like cell 105, while femto RAN 1690 can comprise multiple femtocell access points such as femto AP 130. Deployment density in femto RAN 1690 can be substantially higher than in macro RAN 1670.

Generally, both macro and femto network platforms 1610 and 1680 include components, e.g., nodes, gateways, interfaces, servers, or platforms, that facilitate both packet-switched (PS) (e.g., internet protocol (IP), frame relay, asynchronous transfer mode (ATM)) and circuit-switched (CS) traffic (e.g., voice and data) and control generation for networked wireless communication. In an aspect of the subject innovation, macro network platform 1610 includes CS gateway node(s) 1612 which can interface CS traffic received from legacy networks like telephony network(s) 1040 (e.g., public switched telephone network (PSTN), or public land mobile network (PLMN)) or a SS7 network 1660. Circuit switched gateway 1612 can authorize and authenticate traffic (e.g., voice) arising from such networks. Additionally, CS gateway 1612 can access mobility, or roaming, data generated through SS7 network 1660; for instance, mobility data stored in a VLR, which can reside in memory 1630. Moreover, CS gateway node(s) 1612 interfaces CS-based traffic and signaling and gateway node(s) 1618. As an example, in a 3GPP UMTS network, PS gateway node(s) 1618 can be embodied in gateway GPRS support node(s) (GGSN).

In addition to receiving and processing CS-switched traffic and signaling, PS gateway node(s) 1618 can authorize and authenticate PS-based data sessions with served (e.g., through macro RAN) wireless devices. Data sessions can include traffic exchange with networks external to the macro network platform 1610, like wide area network(s) (WANs) 1650, enterprise networks (NW(s)) 1670 (e.g., enhanced 911), or service NW(s) 1680 like IP multimedia subsystem (IMS); it should be appreciated that local area network(s) (LANs), which may be a part of enterprise NW(s), can also be interfaced with macro network platform 1610 through PS gateway node(s) 1618. Packet-switched gateway node(s) 1618 generates packet data contexts when a data session is established. To that end, in an aspect, PS gateway node(s) 1618 can include a tunnel interface (e.g., tunnel termination gateway (TTG) in 3GPP UMTS network(s); not shown) which can facilitate packetized communication with disparate wireless network(s), such as Wi-Fi networks. It should be further appreciated that the packetized communication can include multiple flows that can be generated through server(s) 1614. It is to be noted that in 3GPP UMTS network(s), gateway node(s) 1018 (e.g., GGSN) and tunnel interface (e.g., TTG) comprise a packet data gateway (PDG).

Macro network platform 1610 also includes serving node(s) 1616 that convey the various packetized flows of information, or data streams, received through PS gateway node(s) 1618. As an example, in a 3GPP UMTS network, serving node(s) can be embodied in serving GPRS support node(s) (SGSN).

As indicated above, server(s) 1614 in macro network platform 1610 can execute numerous applications (e.g., location services, online gaming, wireless banking, wireless device management, . . . ) that generate multiple disparate packetized data streams or flows, and manage (e.g., schedule, queue, format . . . ) such flows. Such application(s), for example can include add-on features to standard services provided by macro network platform 1610. Data streams can be conveyed to PS gateway node(s) 1618 for authorization/authentication and initiation of a data session, and to serving node(s) 1616 for communication thereafter. Server(s) 1614 can also effect security (e.g., implement one or more firewalls) of macro network platform 1610 to ensure network's operation and data integrity in addition to authorization and authentication procedures that CS gateway node(s) 1612 and PS gateway node(s) 1618 can enact. Moreover, server(s) 1614 can provision services from external network(s), e.g., WAN 1650, or Global Positioning System (GPS) network(s), which can be a part of enterprise NW(s) 1680. It is to be noted that server(s) 1614 can include one or more processor configured to confer at least in part the functionality of macro network platform 1610. To that end, the one or more processor can execute code instructions stored in memory 1630, for example.

In example wireless environment 1600, memory 1630 stores information related to operation of macro network platform 1610. Information can include business data associated with subscribers; market plans and strategies, e.g., promotional campaigns, business partnerships; operational data for mobile devices served through macro network platform; service and privacy policies; end-user service logs for law enforcement; and so forth. Memory 1630 can also store information from at least one of telephony network(s) 1640, WAN 1650, SS7 network 1660, enterprise NW(s) 1670, or service NW(s) 1680.

Regarding femto network platform 1680, it includes a femto gateway node(s) 1684, which have substantially the same functionality as PS gateway node(s) 1618. Additionally, femto gateway node(s) 1684 can also include substantially all functionality of serving node(s) 1616. Disparate gateway node(s) 1684 can control or operate disparate sets of deployed femto APs, which can be a part of femto RAN 1690. In an aspect of the subject innovation, femto gateway node(s) 1684 can aggregate operational data received from deployed femto APs. Moreover, femto gateway node(s) 1684, can convey received attachment signaling to attachment component 1620. It should be appreciated that while attachment component is illustrated as external to gateway node(s) 1684, attachment component 1620 can be an integral part of gateway node(s) 1684.

Attachment component 1620 can facilitate macro-to-femto and femto-to-macro handover. In an aspect, NW attachment signaling 240 can be received, processed, and conveyed to a femto AP as a part of attachment procedure among a mobile station and the femto AP. Attachment component 1620 also can receive alarm(s) indication 314, and process, at least in part, such indication to generate a NW response 316 like an indication to restart femto AP; a customer service notification, which can be accomplished through communication with enterprise network(s) 1670 that provides customer service support; indication to display a malfunction indicator . . . ).

Memory 1686 can retain additional information relevant to operation of the various components of femto network platform 1680. For example operational information that can be stored in memory 1686 can comprise, but is not limited to, subscriber intelligence; contracted services; maintenance and service records; femto cell configuration (e.g., devices served through femto RAN 1690; authorized subscribers associated with one or more deployed femto APs); service policies and specifications; privacy policies; add-on features; so forth.

Server(s) 1682 have substantially the same functionality as described in connection with server(s) 1614. In an aspect, server(s) 1682 can execute multiple application(s) that provide service (e.g., voice and data) to wireless devices served through femto RAN 1690. Server(s) 1682 can also provide security features to femto network platform. In addition, server(s) 1682 can manage (e.g., schedule, queue, format . . . ) substantially all packetized flows (e.g., IP-based, frame relay-based, ATM-based) it generates in addition to data received from macro network platform 1610. Furthermore, server(s) 1682 can effect provisioning of femto cell service, and effect operations and maintenance. It is to be noted that server(s) 1682 can include one or more processors configured to provide at least in part the functionality of femto network platform 1680. To that end, the one or more processors can execute code instructions stored in memory 1686, for example.

With respect to FIG. 17, in embodiment 1700, femto AP 1710 can receive and transmit signal(s) from and to wireless devices like macro and femto access points, access terminals, wireless ports and routers, and the like, through a set of antennas $1769_1$-$1769_N$. It should be appreciated that while antennas $1769_1$-$1769_N$ are a part of communication platform 255, which comprises electronic components and associated circuitry that provides for processing and manipulation of received signal(s) and signal(s) to be transmitted. In an aspect, communication platform 255 includes a receiver/transmitter 1766 that can convert signal from analog to digital upon reception, and from digital to analog upon transmission. In addition, receiver/transmitter 1766 can divide a single data stream into multiple, parallel data streams, or perform the reciprocal operation. Coupled to receiver/transmitter 1766 is a multiplexer/demultiplexer 1767 that facilitates manipulation of signal in time and frequency space. Electronic component 1767 can multiplex information (e.g., data/traffic and control/signaling) according to various multiplexing schemes such as time division multiplexing (TDM), frequency division multiplexing (FDM), orthogonal frequency division multiplexing (OFDM), code division multiplexing (CDM), space division multiplexing (SDM). In addition, mux/demux component 1767 can scramble and spread information (e.g., codes) according to substantially any code known in the art; e.g., Hadamard-Walsh codes, Baker codes, Kasami codes, polyphase codes, and so on. A modulator/demodulator 1768 is also a part of operational group 1725, and can modulate information according to multiple modulation techniques, such as frequency modulation, amplitude modulation (e.g., M-ary quadrature amplitude modulation (QAM), with M a positive integer), phase-shift keying (PSK), and the like.

Femto access point 1710 also includes a processor 1735 configured to confer functionality, at least partially, to substantially any electronic component in the femto access point 1710. In particular, processor 1735 can facilitate access management component 235 supplying fixed differentiated QoS in accordance with aspects disclosed herein. In addition, processor 1735 can facilitate operations on data (e.g., symbols, bits, or chips) for multiplexing/demultiplexing, such as effecting direct and inverse fast Fourier transforms, selection of modulation rates, selection of data packet formats, inter-packet times, etc. A memory 1755 can store data structures, code instructions, system or device information like policies and specifications, code sequences for scrambling, spreading and pilot transmission, floor plan configuration, access point deployment and frequency plans, scheduling policies, and so on.

In embodiment 1700, processor 1734 is coupled to the memory 1755 in order to store and retrieve information necessary to operate and/or confer functionality to communication platform 255, access management component 235, and other operational aspects of femto access point 1710.

As it employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Processors can exploit nano-scale architectures such as, but not limited to, molecular and quantum-dot based transistors, switches and gates, in order to optimize space usage or enhance performance of user equipment. A processor may also be implemented as a combination of computing processing units.

In the subject specification, terms such as "data store," data storage," "database," and substantially any other information storage component relevant to operation and functionality of a component, refer to "memory components," or entities embodied in a "memory" or components comprising the memory. For example, information relevant to operation of various components described in the disclosed subject matter, and that can be stored in a memory, can comprise, but is not limited to comprising, subscriber information; femtocell configuration (e.g., devices served by a femto AP; access control lists, or white lists) or service policies and specifications; privacy policies; and so forth. It will be appreciated that the memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), phase change memory (PCM), or flash memory. Volatile memory can include random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). Additionally, the disclosed memory components of systems or methods herein are intended to comprise, without being limited to comprising, these and any other suitable types of memory.

Various aspects or features described herein may be implemented as a method, apparatus, or article of manufacture using standard programming and/or engineering techniques. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD), Blu-ray disc (BD), . . . ), smart cards, and flash memory devices (e.g., card, stick, key drive . . . ).

What has been described above includes examples of systems and methods that provide advantages of the subject innovation. It is, of course, not possible to describe every conceivable combination of components or methodologies for purposes of describing the claimed subject matter, but one of ordinary skill in the art may recognize that many further combinations and permutations of the claimed subject matter are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A femto access point device, comprising:
a memory to store executable instructions; and
a processor coupled to the memory that facilitates execution of the executable instructions to perform operations, comprising:
facilitating a first transmission of request data to a communication device within a coverage area of the femto access point device, wherein the request data is indicative of a request for the communication device to couple to the femto access point device,
in response to receiving, from the communication device, indication data indicative of a rejection of the request, determining timing information representing a time period during which the communication device is to be denied access to the femto access point device, wherein the determining comprises selecting between a first time period representing a temporary denial of femtocell access and a second time period representing a permanent denial of femtocell access,
during the time period, storing identifier data indicative of the communication device within an access control data structure associated with the femto access point device, wherein the access control data structure comprises data indicative of a set of devices that are not authorized to connect to the femto access point device, and
subsequent to the storing, prohibiting a second transmission of the request data to the communication device.

2. The femto access point device of claim 1, wherein the operations further comprise:
scanning a frequency band to facilitate a detection of the communication device in response to the communication device being determined to be located within a coverage area associated with the femto access point device.

3. The femto access point device of claim 1, wherein the operations further comprise:
storing the timing information in the access control data structure.

4. The femto access point device of claim 1, wherein the storing comprises storing the identifier data within the access control data structure based on classification data indicative of a device type associated with the communication device.

5. The femto access point device of claim 1, wherein the storing comprises storing the identifier data within the access control data structure based on historical data indicative of usage history associated with a femto service associated with the femto access point device that has been accessed by the communication device.

6. The femto access point device of claim 1, wherein the operations further comprise:
in response to determining that the time period has expired, deleting the identifier data from the access control data structure.

7. The femto access point device of claim 1, wherein the selecting comprises selecting the first time period and the operations further comprise:
in response to determining that the communication device has exited the coverage area, deleting the identifier data from the access control data structure.

8. The femto access point device of claim 1, wherein the selecting comprises selecting the first time period and the operations further comprise:
in response to determining that an access criterion is satisfied, deleting the identifier data from the access control data structure.

9. The femto access point device of claim 1, wherein the storing comprises storing the identifier data within the access control data structure in response to determining that bandwidth data indicative of a bandwidth availability does not satisfy a bandwidth criterion associated with the femto access point device.

10. The femto access point device of claim 1, wherein the selecting comprises selecting the first time period and the operations further comprise:
in response to determining that the communication device has been restarted, deleting the identifier data from the access control data structure.

11. The femto access point device of claim 1, wherein the selecting comprises selecting the first time period and the operations further comprise:
in response to determining that a battery of the communication device has been discharged, deleting the identifier data from the access control data structure.

12. The femto access point device of claim 1, wherein the storing comprises storing the identifier data within the access control data structure based on policy data indicative of a quality of service policy associated with the communication device.

13. A method, comprising:
in response to determining that a mobile communication device is within a coverage area associated with a femto access point device, facilitating, by the femto access point device comprising a processor, a first transmission of request data from the femto access point device to the mobile communication device, wherein the request data prompts the mobile communication device to access a set of services provided via the femto access point device;
in response to receiving, from the mobile communication device, indication data that indicates that the mobile communication device has denied access to the femto access point device, determining, by the femto access point device, timing information representing a time period during which the mobile communication device is to be denied access to the femto access point device, wherein the determining the timing information comprises selecting between a first time period representing a temporary denial of femtocell access and a second time period representing a permanent denial of femtocell access;
based on the timing information, updating, by the femto access point device, an access control data structure associated with the femto access point device with identifier information associated with the mobile communication device, wherein the access control data structure comprises data indicative of a set of devices that are prohibited to connect to the femto access point device; and
subsequent to the updating, prohibiting a second transmission of the request data to the mobile communication device.

14. The method of claim 13, wherein the updating further comprises adding the identifier data to a slot of the access control data structure.

15. The method of claim 14, wherein the selecting comprises selecting the first time period and the method further comprises:
determining, by the femto access point device, an expiration of the first time period time; and
in response to determining the expiration, deleting, by the femto access point device, the identifier data from the slot.

16. The method of claim 14, wherein the selecting comprises selecting the first time period and the method further comprises:
in response to determining that a battery of the mobile communication device has been discharged, deleting, by the femto access point device, the identifier data from the slot.

17. The method of claim 13, wherein the updating further comprises updating the access control data structure with the identifier information in response to determining that classification data indicative of a type of the mobile communication device satisfies a classification criterion.

18. A non transitory computer-readable storage medium comprising computer-executable instructions that, in response to execution, cause a femto access point device comprising a processor to perform operations, comprising:
directing to a subscriber station device, detected in a coverage area of the femto access point device, request data indicative of a femtocell initiated request that prompts the subscriber station device to access the femto access point device;
in response to receiving reply data from the subscriber station device indicating that the subscriber device has rejected the femtocell initiated request, determining timing information indicative of a time period during which the subscriber station device is to be prohibited from coupling to the femto access point device, wherein the determining comprises selecting between a first time period representing a temporary denial of femtocell access and a second time period representing a permanent denial of femtocell access;
based on the timing information, storing identifier data indicative of the subscriber station device within an access control data structure of the femto access point device, wherein the access control data structure comprises data indicative of a set of devices that are not authorized to connect to the femto access point device; and
subsequent to the storing, denying a transmission of the request data to the subscriber station device.

19. The non transitory computer-readable storage medium of claim 18, wherein the operations further comprise:
in response to determining that the subscriber station device has exited the coverage area, deleting the identifier data from the access control data structure.

20. The non transitory computer-readable storage medium of claim 18, wherein the operations further comprise:
in response to determining that the time period has expired, deleting the identifier data from the access control data structure.

21. A method, comprising:
- receiving, by a communication device comprising a processor, query data from a femto access point device indicative of a request to connect to the femto access point device;
- in response to the receiving, directing, by the communication device, reply data indicative of rejection of the request to the femto access point device, wherein the directing comprises directing the reply data to facilitate storing, during a time period that is determined based on a selection between a first time period representing a temporary denial of femtocell access and a second time period representing a permanent denial of femtocell access, identifier data indicative of the communication device within an access control data structure of the femto access point device that stores data associated with a set of devices that are not authorized to communicate via the femto access point device, and wherein the directing comprises directing the reply data to facilitate, subsequent to the storing, a denial of a transmission of the query data between the femto access point device and the communication device.

22. The method of claim 21, wherein the directing comprises directing, to the femto access point device, policy data that specifies a quality of service policy associated with the communication device and wherein the directing comprises directing the reply data to facilitate the storing based on the policy data.

* * * * *